(12) United States Patent
Douglas et al.

(10) Patent No.: US 9,773,330 B1
(45) Date of Patent: Sep. 26, 2017

(54) SYSTEMS AND METHODS FOR REAL-TIME DATA QUANTIFICATION, ACQUISITION, ANALYSIS, AND FEEDBACK

(71) Applicant: BioMech Sensor LLC, Midlothian, VA (US)

(72) Inventors: John Douglas, Potomac, MD (US); Frank Fornari, Naples, FL (US)

(73) Assignee: BioMech Sensor LLC, Midlothian, VA (US)

( * ) Notice: Subject to any disclaimer, the term of this patent is extended or adjusted under 35 U.S.C. 154(b) by 0 days.

(21) Appl. No.: 15/394,779

(22) Filed: Dec. 29, 2016

(51) Int. Cl.
| | |
|---|---|
| G06T 11/20 | (2006.01) |
| G01C 19/00 | (2013.01) |
| A63B 69/00 | (2006.01) |
| G06F 3/0346 | (2013.01) |
| G06F 3/0484 | (2013.01) |

(Continued)

(52) U.S. Cl.
CPC ........ *G06T 11/206* (2013.01); *A63B 24/0006* (2013.01); *A63B 60/46* (2015.10); *A63B 71/0622* (2013.01); *G06F 3/0346* (2013.01); *G06F 3/04845* (2013.01); *G06F 3/14* (2013.01); *G06T 7/20* (2013.01); *A63B 2024/0012* (2013.01); *A63B 2071/0647* (2013.01); *G06F 3/016* (2013.01); *G06F 3/16* (2013.01); *G06T 2207/30241* (2013.01)

(58) Field of Classification Search
None
See application file for complete search history.

(56) References Cited

U.S. PATENT DOCUMENTS

| | | | |
|---|---|---|---|
| 8,616,989 | B2 | 12/2013 | Bentley |
| 8,821,305 | B2 | 9/2014 | Cusey et al. |

(Continued)

FOREIGN PATENT DOCUMENTS

WO WO 2015/139832 9/2015

OTHER PUBLICATIONS

Zepp Golf User Guide, Mar. 2016, available at https://www.zepp.com/assets/docs.user_guide_zepp_golf.pdf (30 pages).

(Continued)

*Primary Examiner* — Tize Ma
(74) *Attorney, Agent, or Firm* — Finnegan, Henderson, Farabow, Garrett & Dunner, L.L.P.

(57) ABSTRACT

This disclosure relates to systems, media, and methods for quantifying and monitoring exercise parameters and/or motion parameters, including performing data acquisition, analysis, and providing scientifically valid, clinically relevant, and/or actionable diagnostic feedback. Disclosed embodiments may receive real-time sensor data from a motion sensor or sensors mounted on a user and/or equipment while a user performs a test motion. Disclosed embodiments may also calculate a test motion profile based on the real-time sensor data, the test motion profile describing a multi-dimensional representation of the test motion performed by the user or computed motion profiles. Disclosed embodiments may include comparing the test motion profile to a template motion profile to determine a deviation amount for the test motion profile indicating how the test motion deviated from the template motion profile. Still further embodiments may correlate test motion profiles over time with health indicators.

20 Claims, 16 Drawing Sheets

(51) Int. Cl.
*G06F 3/14* (2006.01)
*G06T 7/20* (2017.01)
*A63B 60/46* (2015.01)
*A63B 24/00* (2006.01)
*A63B 71/06* (2006.01)
*G06F 3/01* (2006.01)
*G06F 3/16* (2006.01)

(56) References Cited

U.S. PATENT DOCUMENTS

| | | | |
|---|---|---|---|
| 8,979,665 B1 | 3/2015 | Najafi et al. | |
| 9,044,661 B2 | 6/2015 | Leonard | |
| 9,283,461 B2 | 3/2016 | Parke et al. | |
| 9,339,714 B2 | 5/2016 | Syed et al. | |
| 9,342,994 B2 | 5/2016 | Sato | |
| 9,409,073 B2 * | 8/2016 | Boyd | A63B 69/36 |
| 9,409,074 B2 | 8/2016 | Han et al. | |
| 9,440,127 B2 | 9/2016 | Boggs et al. | |
| 9,449,230 B2 | 9/2016 | Han et al. | |
| 2006/0252018 A1 | 11/2006 | Sooch | |
| 2007/0219744 A1 * | 9/2007 | Kolen | A63B 60/42 |
| | | | 702/150 |
| 2008/0318625 A1 * | 12/2008 | Rofougaran | G01S 13/426 |
| | | | 455/556.1 |
| 2012/0038549 A1 * | 2/2012 | Mandella | G06F 3/03545 |
| | | | 345/156 |
| 2013/0267335 A1 * | 10/2013 | Boyd | A63B 69/36 |
| | | | 473/222 |
| 2013/0296048 A1 | 11/2013 | Jeffery et al. | |
| 2014/0018181 A1 | 1/2014 | Blake et al. | |
| 2014/0357392 A1 | 12/2014 | Goel et al. | |
| 2015/0007658 A1 | 1/2015 | Ishikawa et al. | |
| 2015/0038806 A1 * | 2/2015 | Kaleal, III | A61B 5/4872 |
| | | | 600/301 |
| 2015/0142374 A1 | 5/2015 | Shibuya | |
| 2015/0367174 A1 | 12/2015 | Okazaki et al. | |
| 2016/0001127 A1 | 1/2016 | Sato | |
| 2016/0074741 A1 | 3/2016 | Ramirez | |
| 2016/0086500 A1 * | 3/2016 | Kaleal, III | G06T 19/00 |
| | | | 434/257 |
| 2016/0089566 A1 | 3/2016 | Mitsunaga et al. | |
| 2016/0151696 A1 | 6/2016 | Chen et al. | |
| 2016/0175674 A1 | 6/2016 | Hayaishi | |
| 2016/0175681 A1 | 6/2016 | Inagaki et al. | |
| 2017/0154505 A1 * | 6/2017 | Kim | A41D 1/002 |

OTHER PUBLICATIONS

S. Stancin et al., "Early Improper Motion Detection in Golf Swings Using Wearable Motion Sensors: The First Approach", Received Feb. 28, 2013; Revised May 1, 2013; Accepted Jun. 4, 2013, available at http://nci.nlm.nih.gov/pmc/articles/PMC3715223/ (16 pages).

8 Best Swing Analyzers 2016, Apr. 19, 2016, available at https://www.youtube.com/watch?v=PEApgobMbtl (2 pages).

UberSense: Golf Coach & Swing analysis iPad Review, May 15, 2013, available at https://www.youtube.com/watch?v=d9bsiOtW3T8 (2 pages).

N. Gehrig et al., "Visual Golf Club Tracking for Enhanced Swing Analysis", In *Proceedings of the British Machine Vision Conference (BMVC)* (2003), available at http://cvlabwww.epfl.ch/~lepetit/papers/gehrig_bmvc03.pdf (10 pages).

Swing Profile—State-of-the-art Golf Technology, May 15, 2013, http://www.swingprofile.com/products (last accessed Feb. 14, 2017) (4 pages).

World's Smartest Golf Training Aid and Swing Analyzer Golf App, Dec. 17, 2015, available at https://www.youtube.com/watch?v=SLeGCzmQADY (2 pages).

Arccos Golf—Arccos 360, http://www.arccosgolf.com/pages/arccos-360 (as archived by Archive.org on Dec. 14, 2016) (6 pages).

D. Johnson, "Top golf gadgets to improve your game and swing", Dec. 29, 2016, available at http://gadgetsandwearables.com/2016/12/29/best-golf-wearables/ (20 pages).

* cited by examiner

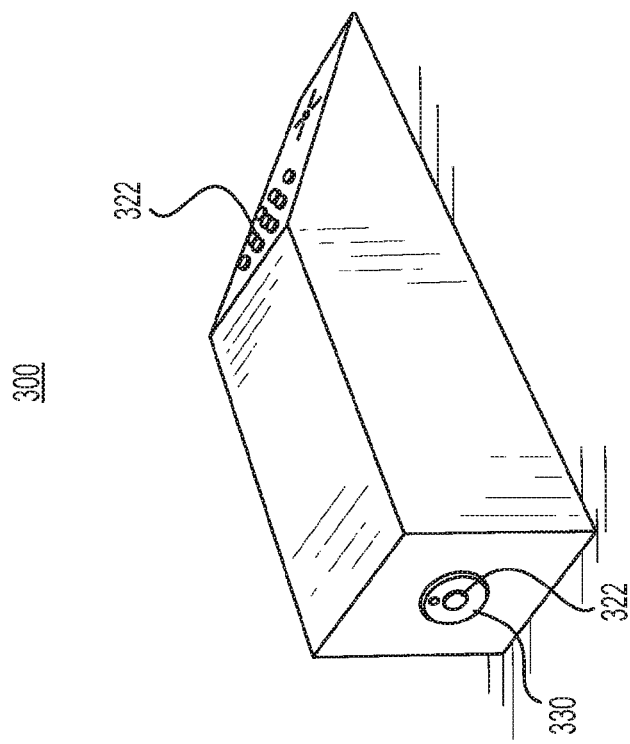
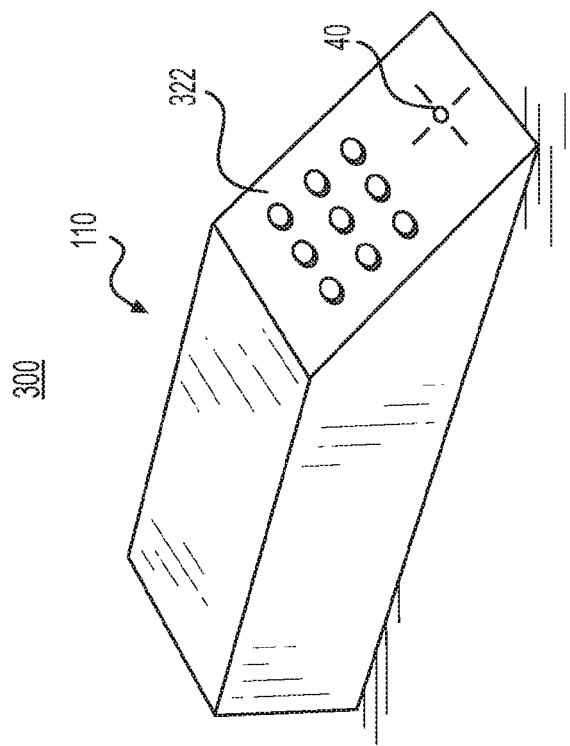
FIG. 3A
FIG. 3B

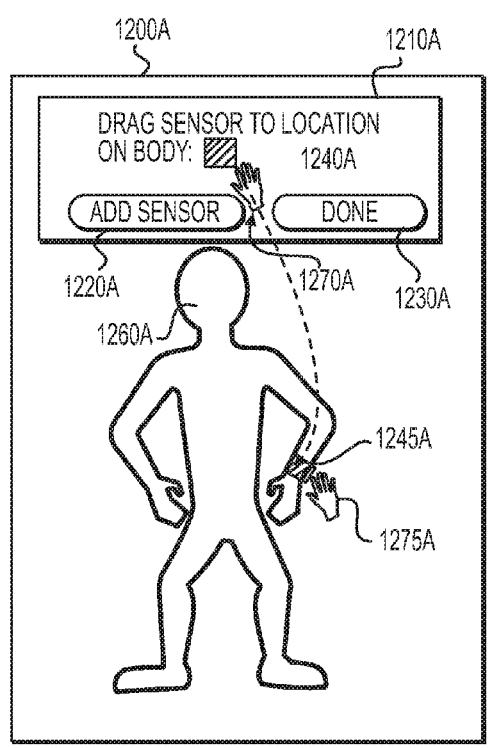 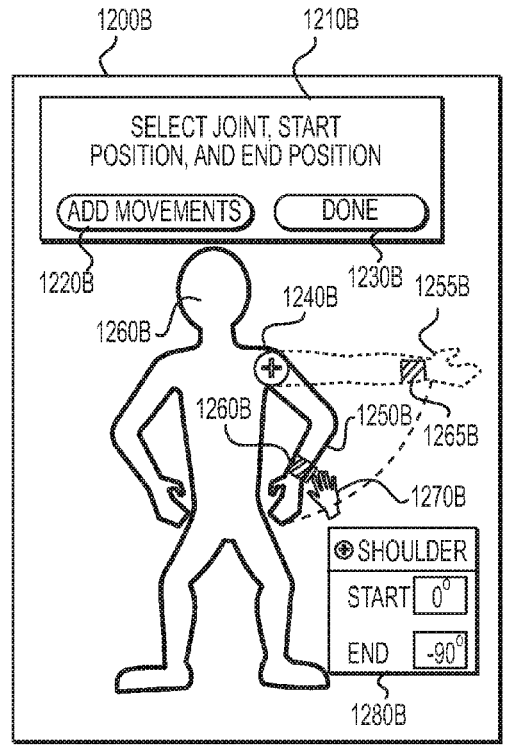
*FIG. 12A*  *FIG. 12B*

SYSTEMS AND METHODS FOR REAL-TIME DATA QUANTIFICATION, ACQUISITION, ANALYSIS, AND FEEDBACK

TECHNICAL FIELD

This disclosure relates generally to data acquisition and analysis, and more particularly to methods and systems for real-time data quantification, acquisition, analysis, and feedback.

BACKGROUND

Existing data acquisition devices include the capability of tracking limited data over time and displaying a status indicator to a user. For example, wrist-worn fitness trackers record and display a user's steps taken over the course of a day. Other devices track a generic amount of activity performed by a user based on a frequency and magnitude of movement. These devices may provide a notification to the user when a target metric is reached. For example, a device may notify a user when the device records a target number of steps or an accumulated activity score.

SUMMARY

Disclosed embodiments may include methods, systems, and computer-readable media to provide near-instantaneous user feedback from real-time golf club sensor data and body worn sensor data. Disclosed embodiments may include loading a template golf swing profile, the template golf swing profile describing a multi-dimensional representation of a motion or orientation over time; receiving real-time sensor data from a motion sensor mounted on a golf club while a user performs a motion with golf equipment, such as a golf swing or golf putts with the golf club or golf putter; calculating a test golf swing profile based on the real-time sensor data, the test golf swing profile describing a multi-dimensional representation of the golf swing performed by the user; comparing the template golf swing profile to the test golf swing profile to determine a deviation amount for the test golf swing profile indicating how the test golf swing deviated from the template golf swing profile; and providing a graphical user interface that displays, and allows the user to manipulate a viewing angle of a multi-dimensional rendering of the test golf swing profile, where the graphical user interface further displays the deviation amount in relation to the multi-dimensional rendering of the test golf swing profile, as well as key metrics of the golf swing or putt performed by the user.

In further embodiments, the motion sensor may be mounted on a shaft of the golf club at or below the base of a grip of the golf club. The embodiments may further include storing the test golf swing profile with a plurality of additional test golf swing profiles, calculating metrics of a test golf swing profile, such as an average test golf swing profile for a given session, determining differences between the average test golf swing profiles over time, dimensionalizing this information according to any and all relevant metadata such as club used, weather, and location, and providing a graphical demonstration of the swing as well as the differences to the user. Additionally, disclosed embodiments may further include providing, responsive to the comparing, real-time feedback to the user through the motion sensor mounted on the golf club based on the deviation amount. Also, disclosed embodiments may further include receiving GPS data, identifying a geographic location based on the GPS data, and indexing the test swing profile according to the geographic location. In other disclosed embodiments, the geographic location may include a golf course and hole number corresponding to the geographic location. In such embodiments, the test swing profile may be indexed according to the identified golf course and hole number, or any other captured meta data as previously suggested.

Disclosed embodiments may include methods, systems, and computer-readable media to provide user feedback based on real-time motion analysis. Disclosed embodiments may include loading a template motion profile or template motion pattern, the template motion profile or template motion pattern describing a multi-dimensional path and including deviation tolerances along the multi-dimensional path; receiving real-time sensor data of a motion performed by a user; calculating a test motion profile based on the real-time sensor data, the test motion profile describing a multi-dimensional path of the motion performed by the user; and responsive to determining that the multi-dimensional path of the test motion profile exceeds a deviation tolerance of the template motion profile, generating a signal to provide feedback to the user.

In disclosed embodiments, the real-time sensor data may be received from one or more inertial motion capture sensors, and the one or more inertial motion capture sensors may capture three-axis acceleration data, three-axis orientation, angular velocity, and gravitational information data over time. In disclosed embodiments, the real-time sensor data may be received from a plurality of co-located inertial motion capture sensors that are compared and/or averaged, the time between receiving the real-time sensor data and generating the signal to provide feedback to the user is less than 40 milliseconds, and the real-time sensor data may have a resolution of at least 10 samples per second.

Disclosed embodiments may include methods, systems, and computer-readable media to provide real-time motion analysis of a sensor wearer to a separate user and allowing the user to provide real-time feedback to the wearer. For example, disclosed embodiments may include loading a template motion profile, the template motion profile describing a multi-dimensional path and including deviation tolerances along the multi-dimensional path; wirelessly receiving real-time sensor data of a motion performed by a wearer of a sensor; calculating a test motion profile based on the real-time sensor data, the test motion profile describing a three-dimensional path of the motion performed by the wearer of the sensor; responsive to determining that the three-dimensional path of the test motion profile exceeds a deviation tolerance of the template motion profile: providing a visual indication to a user in a graphical user interface, an audible indication, or a tactile indication, and presenting the user with a selection area in the graphical user interface to provide feedback to the wearer of the sensor; and responsive to receiving a user selection at the selection area of the graphical user interface, generating a signal to provide feedback to the user.

In disclosed embodiments, the feedback provided to the user may correspond to the portion of the selection area selected by the user. Further, the selection area in the graphical user interface may include: a first selection area to provide tactile feedback to the wearer, and a second selection area to provide visual feedback to the wearer. The selection area may further include: a third selection area to provide audio feedback to the user. Also, the wearer and the user may be located at least 20 yards apart for the duration of the process. Additionally, the wearer and the user may be located 200 yards apart. The wearer and the user may be zero to over 200 yards apart. Further, the wearer and user may be farther than a mile apart so long as a clear line of sight exists between the user and the wear and/or a wire connects the user and the wearer.

Disclosed embodiments may include methods, systems, and computer-readable media to provide an updated motion profile to a user based on motion sensor data of a motion by a user aggregated over time. Disclosed embodiments may include receiving a plurality of sets of motion sensor data of an initial motion performed by a user from a user terminal; loading a target motion profile, the target motion profile describing a three-dimensional path; calculating a plurality of test motion profiles corresponding to the received plurality of sets of motion sensor data, the test motion profiles describing a three-dimensional path of the motion performed by the user; comparing the plurality of test motion profiles to the target motion profile to determine a deviation from the target motion profile over time and an average deviation; responsive to determining that the deviation over time decreases at a rate that is greater than a pre-determined threshold rate or that the average deviation is less than a pre-determined deviation threshold, generating an updated motion profile and instructions for the user to perform an updated motion corresponding to the updated motion profile.

In disclosed embodiments, the updated motion profile may correspond to the initial motion modified to expand over a larger range of motion. Further, the instructions for the user to perform an updated motion include one of an image and a video of a model performing the updated motion.

Disclosed embodiments may include methods, systems, and computer-readable media to facilitate third-party monitoring of user progress. Disclosed embodiments may include receiving a plurality of sets of sensor data of an initial motion performed by a sensor user from a sensor user terminal, wherein the sensor user terminal may include mobile devices, web browsers operating on a computing device, or one or more sensors worn and/or operated by the user or multiple users; loading a template profile, the template profile describing a multi-dimensional path; calculating a plurality of test profiles corresponding to the received plurality of sets of sensor data, the test profiles describing a multi-dimensional path performed by the sensor user or multiple users; comparing the plurality of test profiles to the template profile to determine a deviation from the template profile over time and an average deviation; providing to a third party, using a graphical user interface, a visual indication of the plurality of test profiles in relation to the template profile, the deviation from the template profile over time, and the average deviation, the graphical user interface including a selection area for the third party to provide feedback to the sensor user or multiple users; and responsive to receiving a user selection from the third party at the selection area of the graphical user interface, generating a signal to provide automated feedback to the sensor user or multiple users.

In disclosed embodiments, the feedback to the sensor user may include at least one of: an updated template profile describing a motion and instructions for the sensor user to perform the motion corresponding to the updated template profile, an invitation to schedule an appointment with the third party or an affiliate of the third party, a notification of compliance, non-compliance or thresholding of some attribute or attributes of the motion, or a call request to the sensor user. Also, the providing step may be performed upon request from the third party or responsive to determining that the average deviation exceeds a predetermined threshold. Further, the graphical user interface may highlight particular sensor users based on a test motion profile or a predefined setting, including using color or intensity to reflect selected attributes of the motion information.

Disclosed embodiments may include a system for providing real-time feedback. The system may include one or more sensor devices, and a computing device that may be portable. The one or more sensor devices may include: a processor configured to perform instructions; a memory configured to store instructions; one or more inertial measurement units configured to capture real-time motion data of a motion performed by a user; additional sensors configured to perceive a surrounding environment and transmit sensor data; a transmitter configured to transmit the real-time motion data; a receiver configured to receive feedback; and one or more user feedback mechanisms configured to convey the received feedback to the user. The computing device may include a receiver configured to receive the motion data; a memory configured to store a target motion profile that includes a deviation tolerance; and a processor. The processor may be configured to: calculate a test profile based on the real-time sensor data, the test profile describing a multi-dimensional path of the motion performed by the user; and responsive to determining that the multi-dimensional path of the test motion profile exceeds a deviation tolerance of the template profile, generating a signal to provide feedback to the user. The computing device may further include a transmitter configured to transmit the feedback to the one or more sensor devices. The sensor devices may include feedback mechanisms (e.g., LEDs, tactile feedback, audio feedback, olfactory feedback).

In other embodiments, an interface to virtually generate target profiles for custom motions is provided. For example, a software program may allow a user to create a control set of motion data by selecting the location of the sensor on a computer model of a human body. The user may interact with the computer body model to make the desired motion to create a "target" motion profile for a custom motion. The user interface may provide a display of data over time and receive user instructions to draw bands (start and end time), for each one of the charts to create threshold data (y-axis) and identify patterns (series of actions).

Other embodiments may allow the user to interact with a user interface while wearing one or more sensor devices to record an ideal template motion; the interface may provide a graphical representation of the recorded ideal template motion; and the interface may receive user input modifying the graphical representation of the recorded ideal motion. The graphical representation of the recorded ideal template motion may include a two-axis plot of the sensor data over time. The user input modifying the graphical representation may include the user providing input to the graphical user interface to perform one or more of the following: smoothing selected portions of the recorded ideal template motion and scaling the time and/or amplitude of selected portions of the recorded ideal template motion two-axis plot.

Other embodiments may include a specialized sensor. For example, a sensor device may take the form of an insole. The insole sensor device variant may include sensors not found in other applications, such as multiple pressure sensors to measure running technique or walking technique at different positions. The insole sensor device may also include feedback mechanisms or be combined with a separate feedback mechanism (e.g., a feedback device worn on the waist). Further, disclosed embodiments may include sensors connected to different equipment or machinery, such as a golf club, golf putter, fishing pole, paddle, tennis racket, hat(s), helmet(s), protective padding, glove(s), shoe(s), insole(s), article(s) of clothing, and/or bat. Such sensors may interact with disclosed systems consistent with the functionality of disclosed sensor devices.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIGS. 3A and 3B illustrate views of a sensor device in accordance with some embodiments of the present disclosure.

FIGS. 12A and 12B illustrate real-time data acquisition and feedback graphical user interfaces in accordance with some embodiments of the present disclosure.

DETAILED DESCRIPTION

Figure 1:
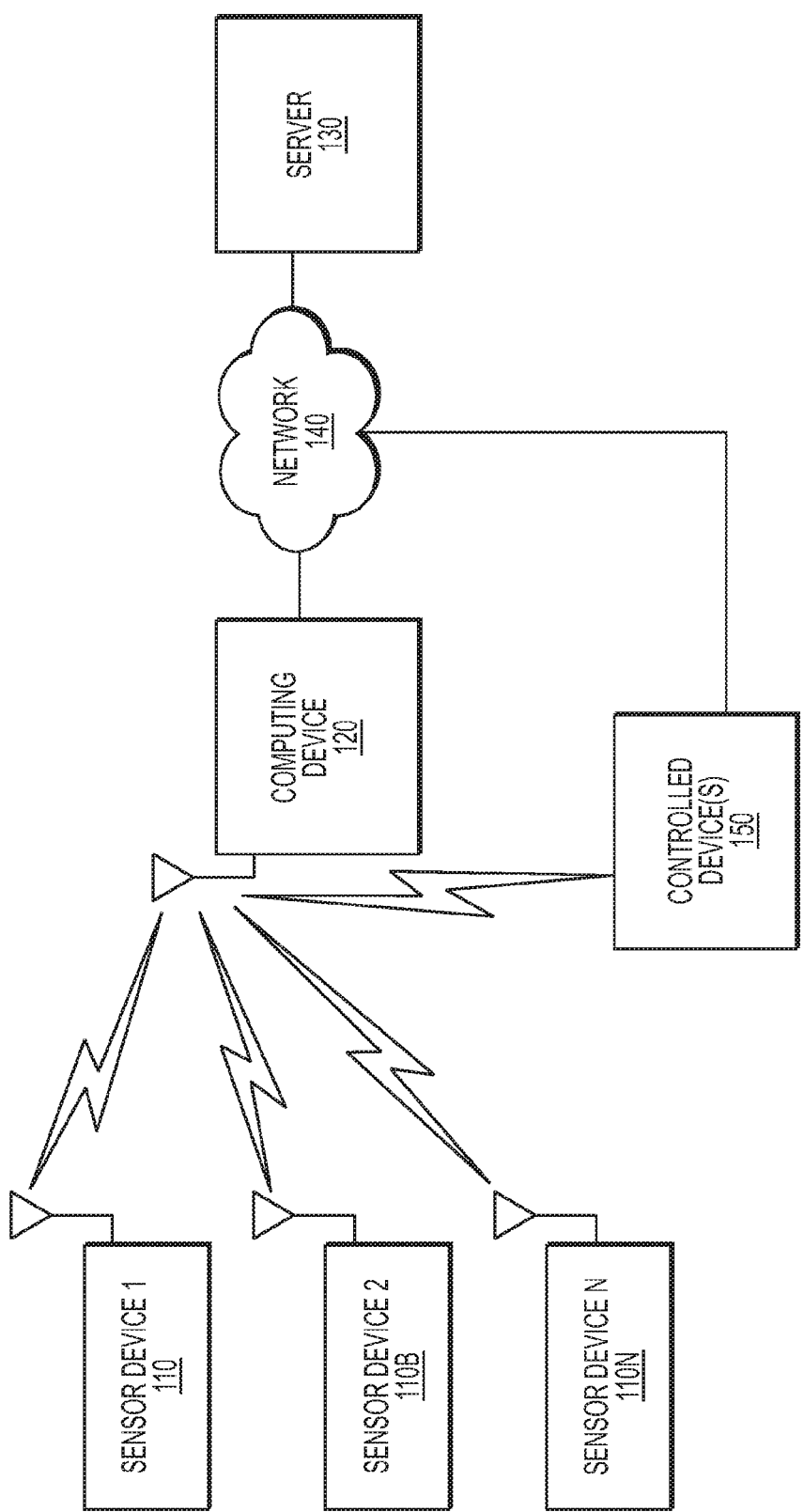
FIG. 1 illustrates an exemplary real-time data acquisition, analysis, and feedback system according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Disclosed embodiments generally relate to systems and methods of acquiring data in real-time, analyzing the data, and providing real-time feedback to the user. Disclosed embodiments may track, quantify, and evaluate body motion of a user and/or equipment or machinery. For example, while moving or exercising, disclosed systems and methods may process sensor data quantifying clinically relevant characteristics of a running stride of a user, as well as evaluate the data by comparing it to simultaneously received data from another user, prior sets of data from the user or other users, and/or model (also referred to as "template") sets of data for a desired running stride. In this example, a user may receive feedback mid-stride or mid-repetition that the movement or action fails to conform to the template set of data. For a single motion or exercise session or for discrete motions performed throughout a session, disclosed systems may provide a quantified measurement of the motion, such as a normalized "score" or percentage deviation between the test and template data sets. Further, over time, disclosed systems may automatically adapt templates based on progress from prior measurements and long-term goals, making sure captured data from a user's motion or motions matches desired criteria, such as orientation, speed, and/or range of motion, for example. Over time, disclosed systems may allow for cloud-based review of progress by the user or a third party (e.g., a healthcare professional), highlighting problematic results that may benefit from specialized treatment, which may include modifications to exercises or instructive motions, different motion instructions altogether, a varied combination of regimens, medication, and/or surgical treatment.

Existing systems and methods may only track a single metric over time. Disclosed embodiments may offer the improved functionality of accounting for and correlating different variables associated with an activity. Disclosed embodiments may offer an improved solution by correlating different tracked data over time and recognizing relevant trends or patterns in the data that may not be apparent without multidimensional correlation.

Existing systems further lack the capability to provide real-time feedback. Disclosed embodiments may offer an improved solution by providing an automatic, immediate, and clinically relevant indication to a user that acquired data fails to match desired characteristics, as well as receiving manual feedback and providing it to the user in real-time. For example, disclosed embodiments may provide real-time feedback to users based on pattern matching algorithms. When received sensor data matches a predefined rule, the sensor or an associated device may provide an indication to the user (e.g., visually, audibly, and/or tangibly). In other examples, real-time data is provided to a third party (e.g., a coach, trainer, doctor, healthcare professional), offering the third party the option to input feedback that systems then transmit to a user in real-time. The relevant real-time feedback, automatic and/or manual, may allow the user to adapt mid-activity, allowing for users to more effectively practice physical movements, for example.

Further, existing systems fail to track changes over time. Disclosed embodiments may offer the improvement of highlighting clinically relevant trends over time between different data profiles. Further, disclosed embodiments may track clinically relevant progress, such as a range of motion or deviation from a template profile. For example, systems and methods may determine that a deviation in a user's walking stride has digressed (e.g., a limp in a user's walk) at a particular magnitude or duration that may present a significant health risk or long-term problem. While such an example may be apparent to the user, exemplary disclosed systems may also uncover latent changes in a user's well-being, such as changes in blood-glucose levels, blood pressure, heart rate, oxidation levels, and hydration, for example. Embodiments may correlate such clinically relevant latent characteristics of a user's body with other activities to note trends of problematic activity. Systems and methods may alert the user and/or a healthcare provider. Moreover, insurance providers may use disclosed systems and methods to offer adapted insurance options tailored to an individual, such as decreasing one's rates for maintaining a lower blood pressure through proper medication, diet, and exercise, or advocating for surgical intervention prior to complete failure of some physiological aspect that would otherwise hamper recovery.

Disclosed embodiments may improve on existing systems by adapting goals, such as to reach a desired outcome and/or based on current results. For example, a user's progress may increase or decrease based on environmental factors and the user's unique physiology. When user performance exceeds planned or expected progress, disclosed embodiments may adapt templates to be more aggressive (e.g., higher range of motion, faster, stronger, longer distances, more repetitions, tighter tolerances to a template). However, if a user's progress stagnates or declines, disclosed embodiments may allow for a more relaxed adaptation of a user's template.

Disclosed embodiments may provide one or more of these improvements. Additional improvements may be present in the embodiments but not explicitly listed here. Further, embodiments need not meet one or more of these outlined benefits to necessarily provide advancement over current technology. Additional advancements are discussed throughout this disclosure.

Disclosed embodiments may include generating, utilizing, and/or manipulating a data profile. In some embodiments, a data profile may be a multidimensional data stream over time or a portfolio of multiple time-synchronized streams of data. A data profile may correlate two or more time-dependent sets of data, such as data received from various sensors. For example, a data profile may represent acceleration in three axes over time. In another example, a data profile may include an accumulated magnitude of movement (e.g., an activity measurement metric) and a recorded blood glucose level over time, or a heartrate, blood pressure, muscle operation, and an activity measurement metric over time. In still further examples, data from electromyography (EMG) sensors, temperature sensors, elevation sensors, light intensity sensors, pressure sensors, force sensors, and electrical sensors may be correlated with health information, such as blood-glucose levels, heartrate, blood pressure, oxygen saturation levels, body temperature, respiratory rate, and/or gait. Other types of data streams may be generated using the sensors and types of data discussed in this specification, consistent with disclosed embodiments. Correlations of performance or health related to elevation, light intensity, temperature, humidity or other external factors are expected.

Disclosed embodiments may include generating, utilizing, and/or manipulating a motion profile. A motion profile may be a data profile that describes the motion of an object, person, and/or extremity over time. A motion profile may include a timewise multidimensional record of motion. For example, motion profiles may include three-dimensional acceleration data, three-axis orientation data, three-axis angular velocity data, and/or three-axis gravitational information over time. In some embodiments, the acceleration and/or orientation data may include data for less than three dimensions, such as single or dual axis acceleration and/or orientation data. The motion profile may combine unique signals of the same motion, such as correlating linear acceleration and angular acceleration.

Based on the motion profile, disclosed embodiments may include rendering a graphical representation of a corresponding motion in space. In the example of a three-dimensional motion profile, disclosed embodiments may include rendering a line in a three-axis space illustrating the path of the object. In still further embodiments, the rendered display may include an animation showing an icon oriented (e.g., based on orientation data) and moving along the path at a rate commensurate with the acceleration data of the motion profile. Such data may also be rendered alongside or overlaid on top of synchronized captured video data.

Disclosed embodiments may include comparing two or more motion profiles or, more generally, data profiles. In some embodiments, systems and methods may determine the magnitude of the differences between two profiles. Such differences may indicate how closely two sets of data match, such as two swings of a golf club. The differences may be quantified using different calculations. In one example, disclosed embodiments may sum the aggregate difference of a fixed period of time (e.g., integrate the differences). Some embodiments may normalize the integrated amount on a per unit time basis. Additionally or alternatively, disclosed embodiments may include comparing two profiles by determining that at a predefined set of points in time (e.g., one or more timewise data points) the two profiles differed by more than a threshold amount (e.g., a predefined threshold or an automatically adjusted threshold).

Disclosed embodiments may include utilizing event models to recognize data profiles, motion profiles, or portions of either that match particular criteria. These criteria may include simple thresholds or complex curve-matching algorithms. In the example of complex curve fitting, an event model may be defined by a specified contour for particular variables of a profile, such that the y-axis displacement (e.g., ordinary least squares difference) or orthogonal distance (e.g., total least squares difference) is below a threshold amount. The amount may be normalized based on the type of application or magnitude of the test profile data.

Disclosed embodiments may use one or more of these concepts individually or in combination as discussed below regarding the figures.

FIG. 1 illustrates an exemplary real-time data quantification, acquisition, analysis, and feedback system 100 according to some embodiments of the present disclosure. System 100 may include one or more sensor devices (110, 110B, 110N), computing device 120, controlled device(s) 150, network 140, and server 130.

System 100 may include one or more sensor devices to aggregate sensor data. Sensor devices 110, 110B, and 110N represent the one or more sensor devices that provide data to system 100. Each of the shown sensor devices may include the same sensor capabilities or different capabilities. For example, sensor 110 may include an inertial measurement unit, while sensor device 110B provides pressure data (e.g., from the grip of a club or racket, or from an insole). In a differing example, the entire sensor shown could only include inertial measurement units, but could be located on different people, or on different points of a single person (e.g., wrist, knee, or ankle). Sensors may provide various sensed data to system 100 as further discussed below.

System 100 may include computing device 120. In some embodiments, computing device 120 may be a general purpose computer, tablet device, smartphone, or smart watch. Computing device 120 may include a processor, memory (e.g., RAM, flash memory, and/or a hard disc), various wired and wireless interfaces (e.g., Bluetooth, IEEE 802.11, Ethernet, USB, USB-C, and/or proprietary ports such as Apple Lightning), input devices (e.g., touchscreen, keyboard, mouse), and a display. Computing device 120 may operate programmable instructions stored locally or remotely to perform disclosed processes.

Computing device 120 may interact with one or more sensor devices. Computing device 120 may receive sensor data from sensor device 110, sensor device 110B, and/or sensor device 110N. For example, sensor device 110 may send, in real-time, data perceived from sensors. Sensor data may be high-resolution data, and the connection between sensor device 110 and computing device 120 may be a high-bandwidth connection, such as a Bluetooth "classic" wireless connection. While such high-bandwidth wireless technologies may use more power than alternatives (e.g., Bluetooth "low energy"), the increased data resolution that may be used by system 100 may require higher bandwidth wireless interfaces.

System 100 may include controlled device(s) 150 that perform functions based on received instructions. For example, controlled device(s) 150 may include output devices, such as remote displays, speakers, and tactile engines that provide feedback to a user of sensor device 110. These types of controlled devices may provide a status indicator to the user based on the sensor data, such as informing the user that the sensor device is providing a data profile that meets expectations by displaying a green light, playing a positive tone, or tapping the user via a worn tactile engine.

In another example, controlled device(s) 150 may include devices that affect a user's workout environment. For example, controlled device(s) may include a fan, air conditioning system, or workout equipment. In this example, computing device 120 may transmit instructions to increase a fan speed and/or activate an air conditioner responsive to determining that the sensor device 110 indicates that a user's body temperature exceeds a healthy threshold level.

In still other examples, controlled device(s) 150 may include medical devices, such as insulin pumps, pacemakers, cardiac defibrillators, gastric stimulators, deep brain neurostimulators, and/or cochlear implants. In one example, computing device 120 may transmit a control signal to an insulin pump to vary insulin dosage based on data from sensor device 110 indicating higher levels of activity (e.g., a data profile matching an event model for intensifying activity). In another example, computing device 120 may transmit a control signal to a medication pump to provide medication to prevent or greatly lessen Parkinsonian tremors.

System 100 may include network 140. In some embodiments, network 140 may be a wired and/or wireless network. For example, network 140 may be a LAN, WAN, WLAN, or the Internet. System 100 may use network 140 to connect various devices. For example, computing device 120 may connect to server 130, controlled device(s) 150, and/or sensor device 110 using the network. Alternatively, as depicted, computing device 120 may interface directly with sensor device 110 and/or controlled device(s) 150. For example, computing device 120 may form its own wireless access point to connect to other devices.

System 100 may include server 130 to provide networked storage and analysis. Server 130 may be a networked computer. Server 130 may include a central processing unit, such as at least one data processor that executes program components for executing user- or system-generated requests. The processor may include specialized processing units or a general purpose microprocessor.

Server 130 may facilitate network-based (e.g., "cloud") storage and data interaction. For example, computing device 120 may transmit data profiles and the underlying raw data to server 130 for storage. In an embodiment, server 130 may analyze data profiles over time and provide feedback based on changes. Server 130 may transmit notifications (e.g., send email, upload data, revise websites, update databases) based on analysis of data.

In some embodiments, server 130 may serve as a portal to allow users to interact with archived data profiles and raw data. For example, server 130 may provide a graphical user interface that presents data profiles organized by particular categories, dates, or types.

Figure 2:
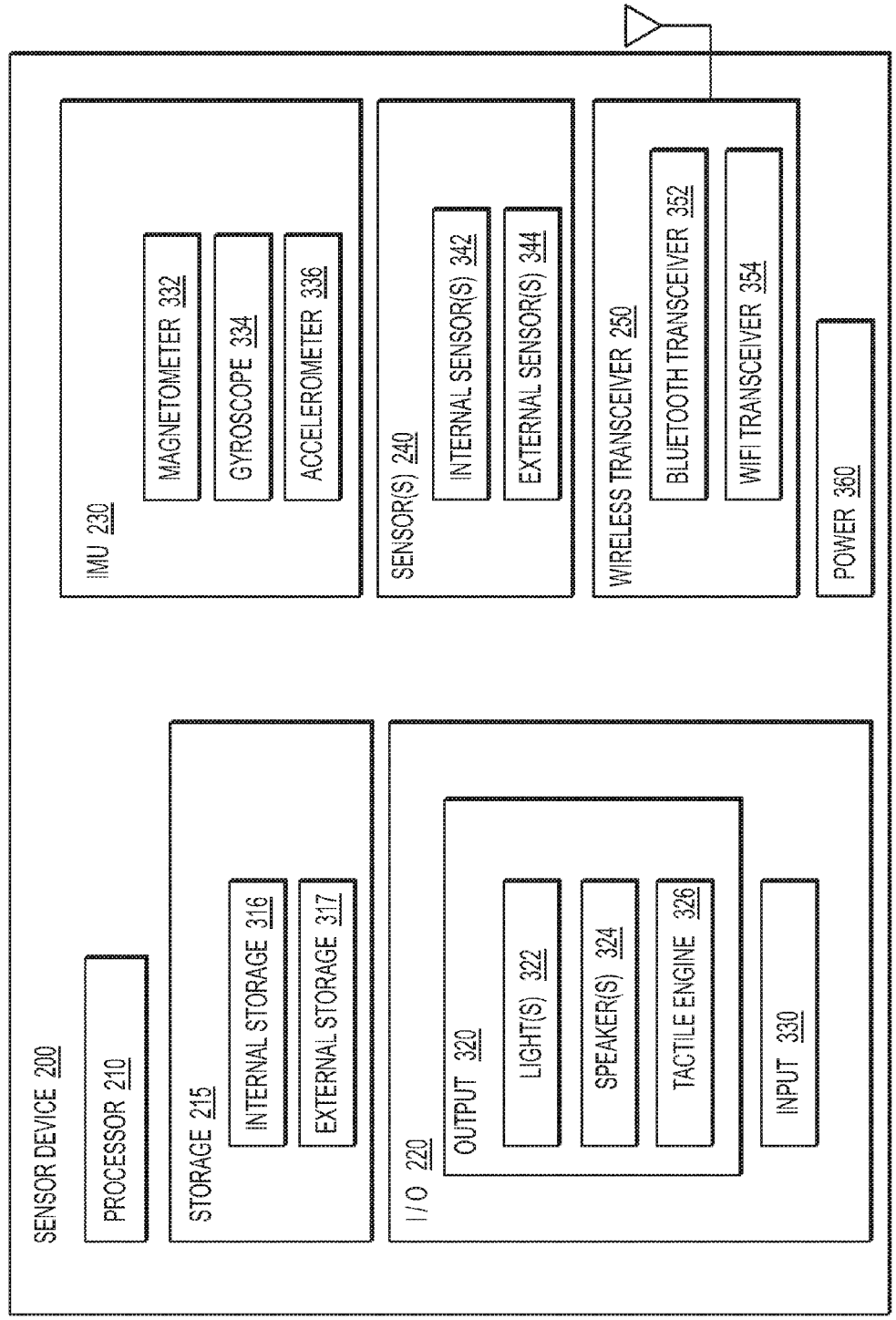
FIG. 2 is a functional block diagram of a sensor device according to some embodiments of the present disclosure.

FIG. 2 is a functional block diagram of sensor device 200 according to some embodiments of the present disclosure. Sensor device 200 may be an example of sensor device 110, consistent with disclosed embodiments. Sensor device 200 may include processor 210, storage 215, input-output 220, IMU 230 (inertial measurement unit), sensor(s) 240, wireless transceiver 250, and/or power 360.

In some embodiments, processor 210 may be a general purpose processor, programmable microcontroller, programmable processor (e.g., a field-programmable gate array (FPGA) or complex programmable logic device (CPLD)), or an application specific integrated circuit (ASIC).

In some embodiments, storage 215 may include internal storage 316 and/or external storage 317. Internal storage 316 may include, for example, on-board memory, such as flash memory or RAM. External storage may include, for example, removable memory media, such as compact flash cards, secure digital cards, memory sticks, optical disks, and the like. In some embodiments, storage 215 may include non-transitory computer-readable media that stores instructions that, when executed by a process (e.g., processor 210), cause the processor to perform disclosed functions and processes.

Input-output 220 may include output 320 and input 330. In some embodiments, output 320 may include lights 322 (e.g., on or more LEDs, an LCD display, a laser, a projector), speaker(s) 324 (e.g., a piezoelectric speaker, a buzzer, a siren, a loudspeaker), and tactile engine 326 (e.g., vibrators, haptic feedback mechanisms). Lights 322 may include lights on various surfaces and different angles of sensor device 200.

Input 330 may allow a user to activate and interact with sensor device 200. In some embodiments, input 330 may include a physical input mechanism (e.g., button, switch, capacitive interface) or a way to receive input (e.g., an infrared receiver, an optical receiver, a USB or serial port). Physical input mechanisms, for example, may allow the user to turn sensor device 200 on and off, synchronize with a computing device, and/or change modes.

As an example of types of arrangements of output 320 and input 330, FIGS. 3A and 3B illustrate views of sensor device 300 (e.g., an exemplary sensor device 110 and/or sensor device 200) in accordance with some embodiments of the present disclosure. In some embodiments, sensor device 300 may include a combination of lights, such as an LED array. For example, as shown, sensor device 300 includes an angled face with a grid of lights 322 (e.g., LEDs). This grid may be programmed to display low resolution patterns or provide greater intensity light as a single unit. On another face, sensor device 300 may include a light combined with an input device (e.g., light(s) 322 combined with input 330 on the opposite face of sensor device 300). For example, input 330 may be a physical button that a user may press to interact with sensor device 300. Various depression patterns (e.g., long-press, double-press, triple-press, quick-press) may be used to indicate different input codes. For example, a user may long press the button to initiate pairing with a computing device 120. In another example, a user may tap a code corresponding to a tag that the user wishes to associate with a particular set of data collected. The user may, for example, triple tap input 330 before and/or after performing a motion to indicate that system 100 should flag the corresponding motion profile as an "ideal" or template motion, or a particular motion of interest for further analysis (e.g., bookmarking). While input 330 is shown as a single button, additional buttons (not shown) may be placed adjacent to input 330 or on different faces of sensor device 300. In addition to physical buttons, sensor device 300 may include receiver 40 to receive infrared or optical input, for example.

Returning to FIG. 2, in some embodiments, sensor device 200 may include IMU 230 to capture multi-dimensioned acceleration and orientation data. IMU 230 may include magnetometer 332, gyroscope 334, and/or accelerometer 336. In certain embodiments, processor 210 may sample IMU acceleration and orientation data at a rate of 100 samples per second. In some embodiments multiple IMU devices may be "stacked" and then time sliced to permit N Factor sample rate increases such that two such devices can generate 200 samples per second or even more.

In some embodiments, sensor device may include multiple instances of IMU 230 as a redundant measure to filter outlying measurements. For example, processor 210 may receive three-axis acceleration data from two or more IMUs. Processor 210 may average the acceleration data to increase accuracy, or when there are three or more IMUs, processor 210 may not make use of the highest and lowest readings, averaging the remaining readings to reduce measurement inaccuracies.

Sensor device 200 may also include various sensor(s) 240. In some embodiments, sensors may be embedded in sensor device 200 as internal sensor(s) 342. For example, a temperature sensor, light intensity sensor, humidity sensor, elevation sensor, and/or microphone may be housed within sensor device 200 and may interface directly with processor 210. In some embodiments, sensors may interface with sensor device 200 through a port or physical interface as external sensor(s) 344. For example, through a USB or serial connection, sensor device 200 may receive data from off-board sensors, such as biopotential telemetry measurement devices (e.g., electrocardiogram (ECG), electroencephalogram (EEG), electromyogram (EMG) data), optical input devices (e.g., cameras, rangefinders), and/or smartphone sensors (e.g., smartphone GPS, elevation, time, weather, sound, light). In some embodiments, external sensor(s) 344 may be used to verify data from internal sensor(s) 342.

Sensor device 200 may include wireless transceiver 250. Transceiver 250 may facilitate communication with computing device 120, network 140, and/or controlled device(s) 150. In some embodiments, transceiver 250 may include Bluetooth transceiver 352 and/or Wi-Fi transceiver 354. In an example, Bluetooth transceiver 352 may be a Bluetooth "classic" transceiver, rather than a Bluetooth "low energy" transceiver in order to provide increased bandwidth to transmit high resolution sensor data (e.g., to computing device 120) in real-time. In another example, Wi-Fi transceiver 354 may be an IEEE 802.11a/b/g/n/x transceiver. Additional wired and/or wireless standards may be used consistent with the bandwidth requirements of the disclosed systems and processes.

Sensor device 200 may include power 360 to provide electricity to components, such as processor 210 and storage 215, among other elements. In some embodiments, power 360 may include a direct current power source, such as a battery. For example, power 360 may include a lithium ion polymer (LiPo) battery, nickel-metal hydride (NiMH) battery, and/or a nickel-cadmium battery. When power 360 includes a battery, power 360 may further include recharging circuitry, such as an electrical port, a removable battery, and/or inductive charging circuitry.

FIGS. 4A, 4B, 4C, and 4D illustrate different equipment with a sensor device according to some embodiments of the present disclosure.

Figure 4A:
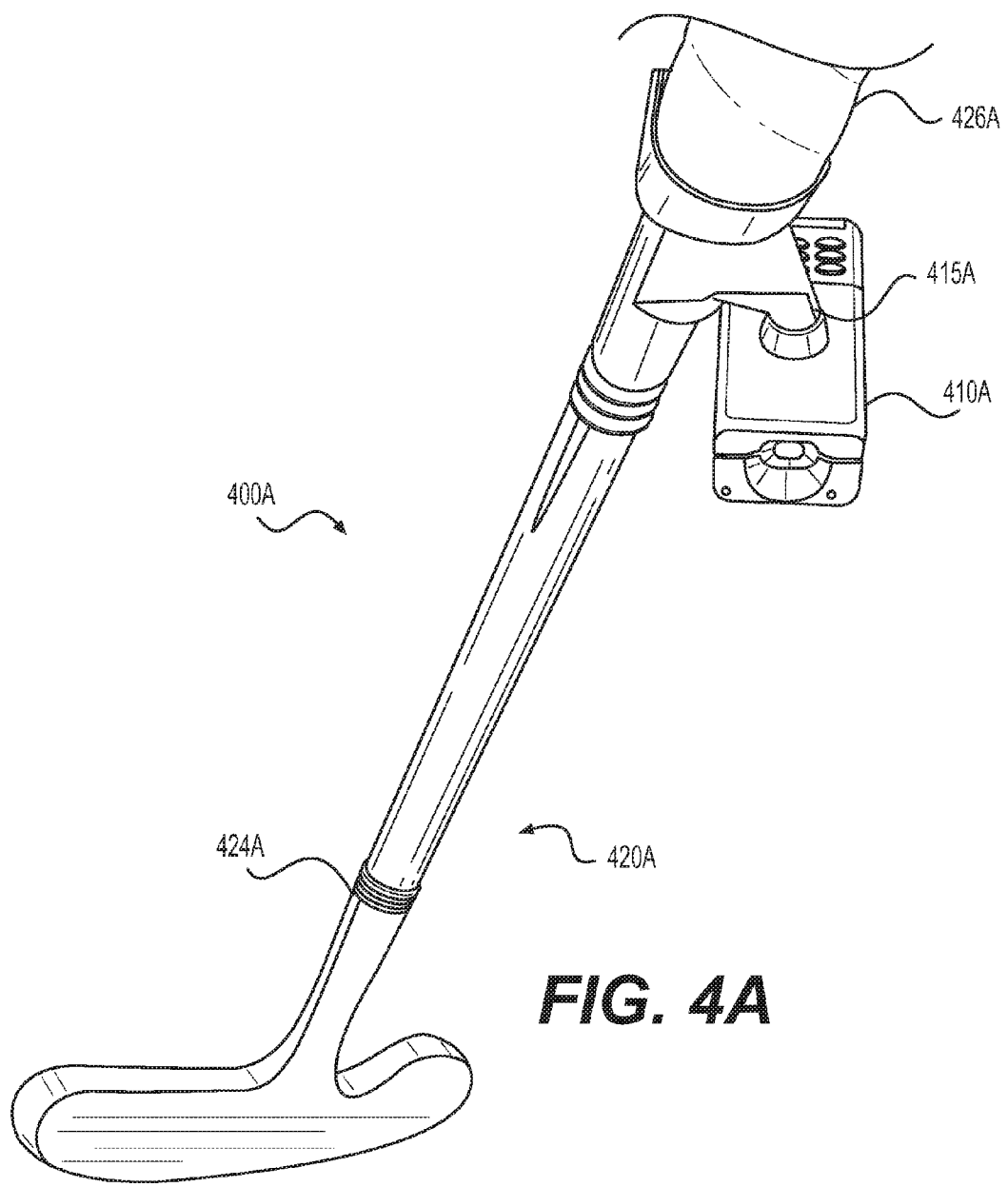
FIGS. 4A, 4B, 4C, and 4D illustrate different equipment with a sensor device in accordance with some embodiments of the present disclosure.

Turning to FIG. 4A, system 400A includes golf club 420A with sensor device 410A. Golf club 420A may be a conventional golf club, such as a putter, driver, or pitching wedge. Golf club 420A may include head 424A and grip 426A.

Sensor device 410A (e.g., sensor 110) may attach to golf club 420A. In some embodiments, mount 415A may be used to secure sensor device 410A to golf club 420A. While a golf putter is shown, additional club heads, such as drivers, fairway woods, hybrid clubs, irons, and pitching wedges may all serve as golf club 420A. As shown, sensor device 410A may connect to golf club 420A at the base of grip 426A. This positioning of sensor device 410A may advantageously provide more accurate inertial data of the swing motion. For purposes of this discussion, "swing" may refer to the motion of teeing off with a driver, swinging a nine iron on a fairway, and/or putting with a putter, for example. Additionally, placement at the base of grip 426A may allow users to swing golf club 420A without sensor device 410A interfering with their line of sight. However, in other embodiments, sensor device 410A may be mounted at other position on golf club 420A. In still other embodiments, multiple sensor devices may be mounted at different positions of golf club 420A, such as near head 424A, along the shaft, and/or at various locations on grip 426A.

In an embodiment, grip 426A may capture pressure data through the use of pressure sensors. For example, grip 426A may include one or more embedded, attached, or otherwise added pressure sensors. The pressure sensors may record the pressure of the user's grip during use of the club. Such data may be useful in providing relevant, real-time feedback to users while practicing. For example, the grip sensors may also include a feedback mechanism (e.g., tactile engine, light, or speaker) that notifies a user when he or she is gripping the club too tightly, which may negatively impact one's swing. This notification may occur at the exact moment that the pressure sensors sense the club is being gripped too tightly, for example, prior to swinging and/or during a golf swing. Alternatively, the feedback mechanism may be programmed to notify a user that the user's grip was too tight after completion of a golf swing, either automatically, or in response to a user request for feedback and/or sensor data.

To provide the data to system 100, such pressure sensors may form an independent sensor device (e.g., a version of sensor device 110). For example, the grip sensor may independently transmit data over a wireless connection (e.g., a Bluetooth connection) to computing device 120. Similarly, an independent grip sensor device may participate in a sensor mesh network to send data through system 100. Alternatively, the grip sensor(s) may interface with sensor device 410A (e.g., as one or more external sensor(s) 344) to provide the grip pressure data to system 100. For example, the grip sensor may transmit data to processor 210 for handling via an external sensor interface in sensor 110.

Figure 4B:
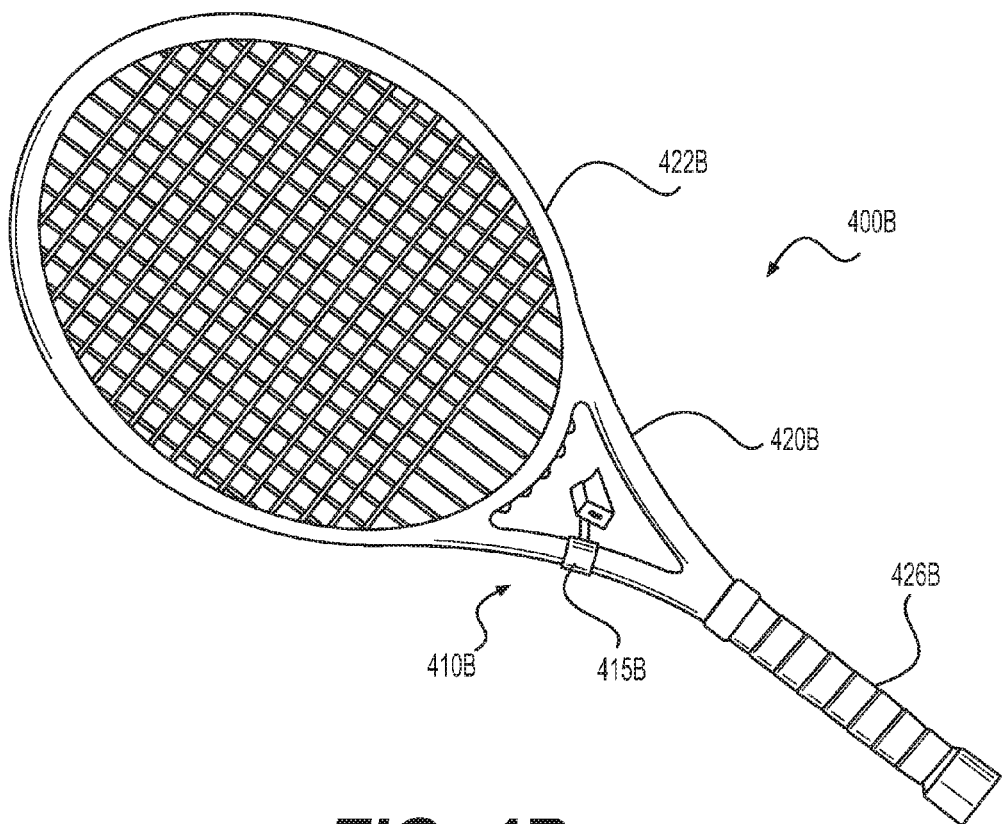

Turning to FIG. 4B, system 400B may include racket 420B with sensor device 410B. Racket 420B may be a conventional racket with head 422B and grip 426B.

Similar to system 400A, in system 400B, sensor device 410B (e.g., sensor device 110) may attach to racket 420B. In some embodiments, mount 415B may be used to secure sensor device 410B to racket 420B. As shown, sensor device 410B may connect to racket 420B between grip 426B and head 422B. This positioning of sensor device 410B may advantageously "hide" sensor device 410B from the line of sight of the user while he or she operates racket 420B. In still other embodiments, sensor device 410B may be mounted at a different position on racket 420B, such as at the top of head 422B, along the shaft, and/or on grip 426A.

Further, as explained above with regard to grip 426A of FIG. 4A, grip 426B may include one or more sensors to measure a user's grip. For example, one or more sensors may measure pressure on grip 426B from the user holding racket 420B, such as generating a pressure map of the user's grip. This may advantageously allow system 100 to determine how the user is holding racket 420B including, for example, determining the relative angle of the face of head 422B relative to the hand or hands of the user. This may allow system 100 to evaluate how the grip angle (e.g., angle with regard to the rotation of the axis of the grip) and pressure affects, for example, serve speed, placement, and spin.

Figure 4C:
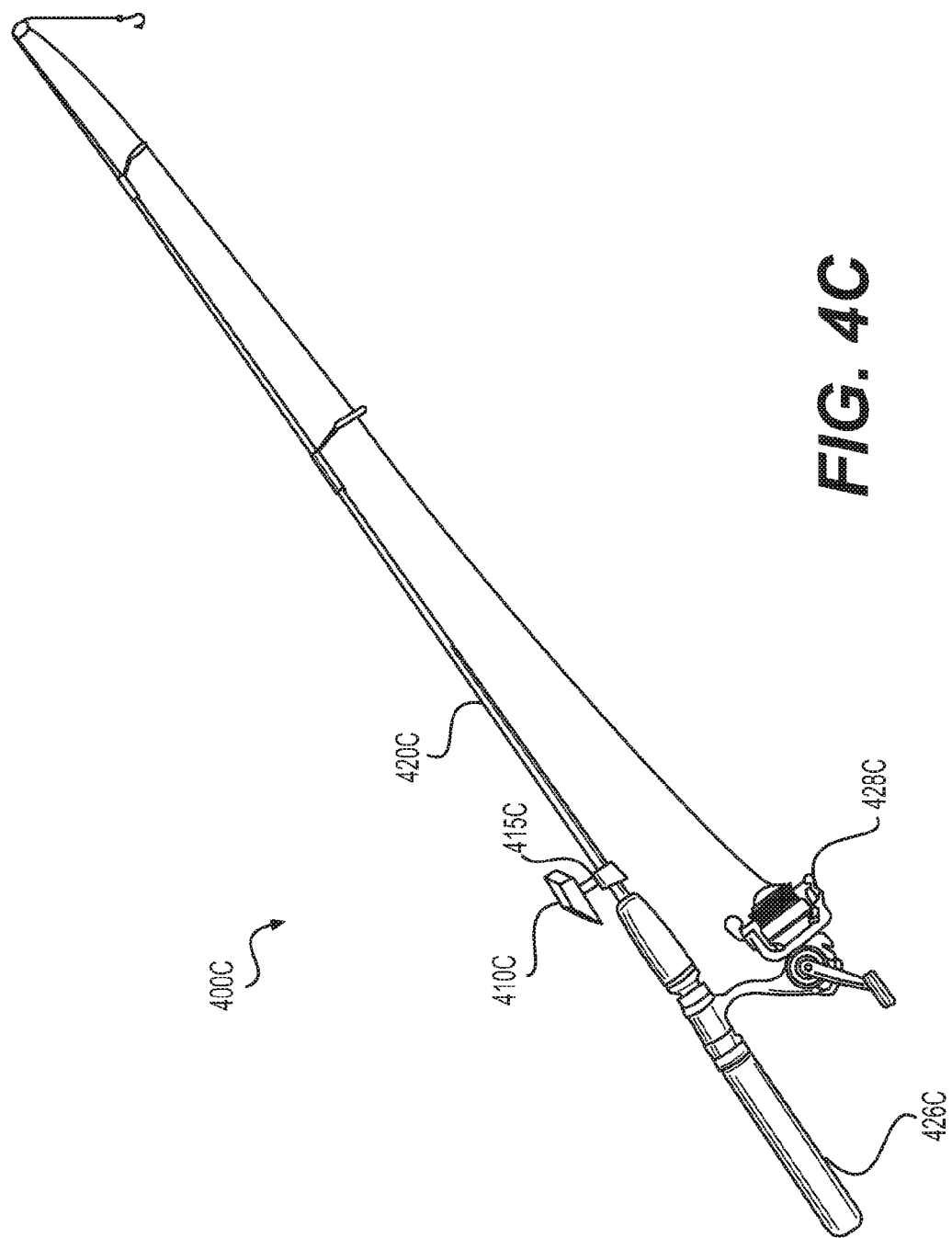

In FIG. 4C, system 400C may include fishing rod 420C and sensor device 410C. Fishing rod 420C may be a conventional fishing pole (e.g., for fly fishing or deep sea fishing. As shown, fishing rod may include reel 428C and handle 426C. Although not explicitly shown, fishing rod 420C may include additional lures and additional guides along the ferrule.

Similar to system 400A, in system 400C, sensor device 410C (e.g., sensor device 110) may attach to fishing rod 420C. In some embodiments, mount 415C may be used to secure sensor device 410C to fishing rod 420C. As shown, sensor device 410C may connect to fishing rod 420C where handle 426C meets the ferrule. This positioning of sensor device 410C may advantageously place sensor device 410B out of areas where an angler typically manipulates fishing rod 420C. For example, the depicted sensor device placement allows a user to freely operate reel 428C and does not interfere with the line. In still other embodiments, sensor device 410C may be mounted at a different position on fishing rod 420C, such as along the rod or ferrule, or integrated into reel 428C or handle 426C.

Further, as explained above with regard to grip 426A of FIG. 4A and grip 426B of FIG. 4B, handle 426C may include one or more sensors to measure a user's grip. For example, one or more sensors may measure pressure on handle 426C from the user holding handle 426C. This may advantageously allow system 100 to determine how stiffly the user is holding fishing rod 420C for evaluating how the grip and pressure affects casting technique.

Additionally, while not shown in FIG. 4C, fishing rod 420C may have additional sensors, either embedded or mounted) to measure action of reel 428C and/or tension in the fishing line. Further, sensor devices may be embedded in the hook or fly at the end of the fishing line. Based on this additional data system 100 may generate a data profile that correlates the casting motion (e.g., from IMU data of sensor device 410C) with reel action, line tension, and fly movement. These combined timewise variables may be used to provide real-time feedback to a user to improve casting motions. For example, system 100 may activate a light or vibration to indicate to the user that the cast motion is too aggressive or oscillates too quickly. Additional combinations of sensors and resulting data may be used consistent with the disclosed embodiments to provide additional user feedback and analysis.

Figure 4D:
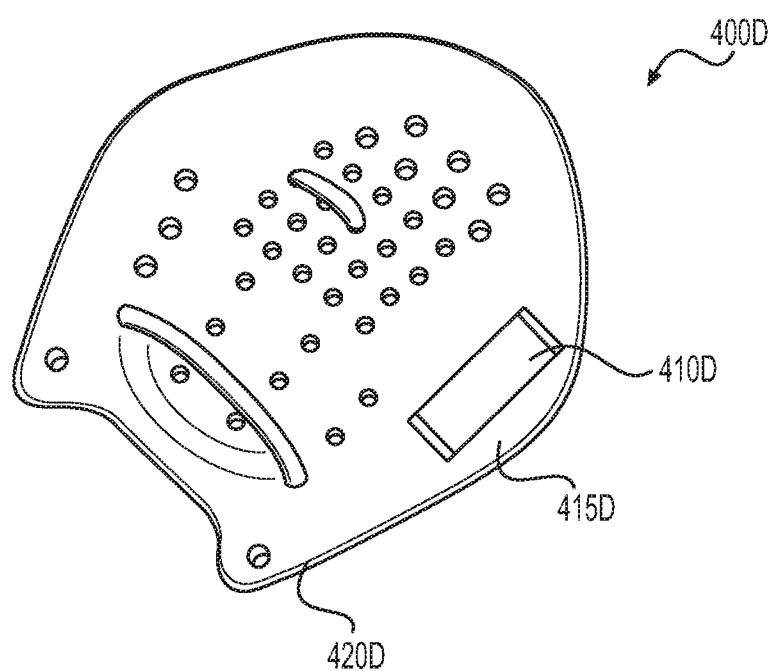

Turning to FIG. 4D, system 400D may include paddle 420D and sensor device 410D. As shown, paddle 420D may be swimming paddle with bands to mount to a swimmer's hand. However, paddle 420D may also be a paddle oar for boating, such as a canoe, stand-up paddleboard, or crew rowing.

In system 400D, sensor device 410D (e.g., sensor device 110) may attach to paddle 420D. In some embodiments, mount 415D may be used to secure sensor device 410D to paddle 420D. Alternatively, sensor device 410D may be integrated into paddle 420D.

Additionally, while not shown, additional sensor units may be used. For example, additional sensors may measure the pressure of water or the user's hand or against a face of paddle 420D. Such sensor data may be used to generate a pressure map of the face of paddle 420D. Based on the sensor data, system 100 may provide feedback on the orientation of paddle 420D during a stroke. For example, in the context of crew rowing, the paddle may be less efficient when its face is not held perpendicular to the direction of the row. The calculated pressure map may reveal points at which the water is not being effectively pulled (or pushed), and system 100 may provide user feedback to adjust the orientation to provide maximum pulling (or pushing) power in the water.

While not shown in FIGS. 4A through 4D, sensor device 110 may be attached to other equipment, such as apparel (e.g., belts, bracelets, shirts, shoes), walking assistance devices (e.g., canes, walkers, scooters, crutches), prosthetics (e.g., hand, arm, leg prosthetics), tools (e.g., hammer, spatula, scalpel), and/or fitness equipment (e.g., medicine balls, jump ropes, helmets, elastic bands).

Figure 5:
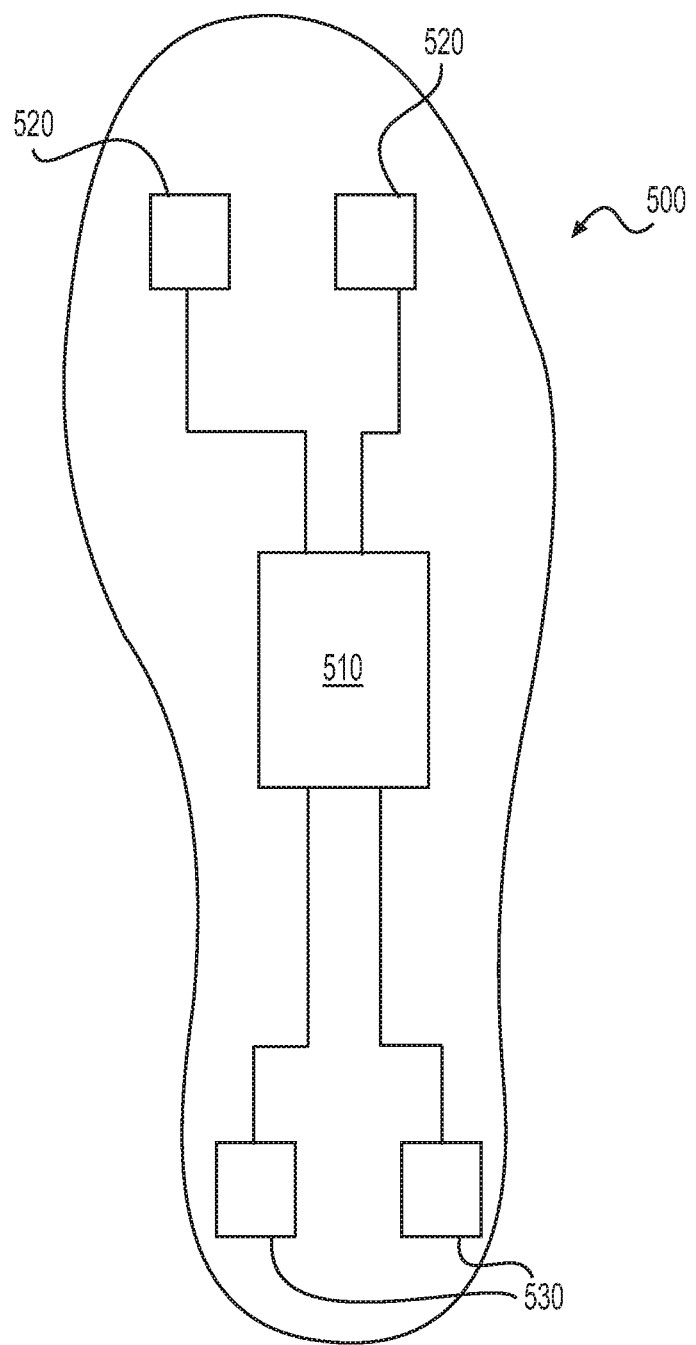
FIG. 5 is a block diagram for a footwear sensor device according to some embodiments of the present disclosure.

FIG. 5 is a block diagram for a footwear sensor device system 500 according to some embodiments of the present disclosure. As shown, sensor device 510 (e.g., sensor device 110) may be embedded into an insole or in a flat flexible sheet that fits below an insole in footwear.

In some embodiments, various pressure sensors may interface with sensor device 510. As shown, toe sensor devices 520 and heel sensor device 530 may connect to sensor device 510 (e.g., as external sensor(s) 344). As shown, four pressure sensors may be located at each corner of system 500 to determine pressure in two-dimensions. Based on the multi-dimensional pressure data, system 100 may generate a pressure map, and provide feedback to the user in real-time to improve stride, gait, pronation, and cadence. For example, various parts of output 320 may be used to indicate to the user that cadence should increase or to shorten stride length, while one is running or walking.

Figure 6:
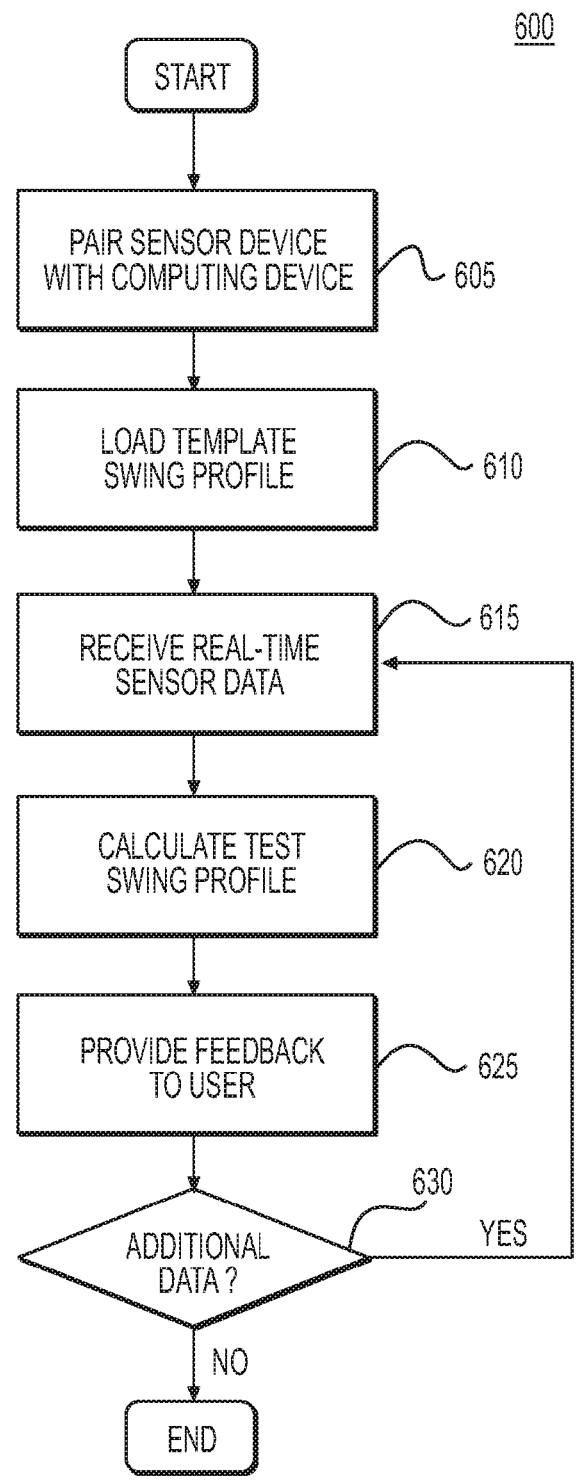
FIG. 6 is a flow diagram illustrating a real-time data acquisition and feedback process in accordance with some embodiments of the present disclosure.

FIG. 6 is a flow diagram illustrating a real-time data acquisition and feedback process in accordance with some embodiments of the present disclosure. Steps in the following discussion may be described with regard to the actions performed by computing device 120. However, one or more alternative devices may instead perform the disclosed functions. For example, in an embodiment, sensor device 110 may perform certain data aggregation, calculation, and/or feedback functions locally (e.g., step 610, step 615, step 620, step 625, and/or step 630). Additionally, while the steps of process 600 are shown in a particular order, the individual steps may be reordered or omitted.

Process 600 may be combined with step 605, where system 100 pairs one or more instances of sensor device 110 with computing device 120. In some embodiments, sensor device 110 may initiate a connection to computing device 120 based on input from a user (e.g., using input 330, such as pressing a button). For example, sensor device 110 may utilize a Bluetooth pairing procedure or connect to computing device 120 via a Wi-Fi connection. In some embodiments, computing device may search or look for sensor devices that are trying to connect or available for connection.

In some embodiments, step 610 may include a calibration procedure. Sensor device 110 may calibrate sensors, such as IMU 230, prior to pairing with computing device 120. For example, sensor device 110 may provide an indication to a user (e.g., a flashing light of lights 322) to indicate to a user to rotate sensor device 110 so that IMU 230 may align its axes and adjust scaling factors to increase accuracy in position and orientation calculations. In other embodiments, calibration may occur during or after pairing, such as when system 100 determines that the data from IMU 230 lacks necessary precision.

In step 610, process 600 may load a template swing profile. The term "swing profile" as used in this disclosure may refer to various golf motions, including swinging a driver, performing a chip shot, and/or putting with a putter, for example. The terms "putt profile" and "swing profile" may be used interchangeably. Computing device 120 may retrieve a data profile (e.g., a motion profile) to serve as a template or pattern for comparing purposes. The data profile may include multi-dimensional acceleration and/or orientation data corresponding to a golf swing. In an embodiment, the template swing profile may be recalled from local or network storage. For example, computing device 120 may request a particular template swing profile from server 130 or other cloud storage.

In an embodiment, loading a template swing profile (step 610) may include recording one or more motion profiles for an actual swing. For example, a user may provide an initial motion at the start of a practice session that acts as a template and may want to practice repeating that initial, template motion. To record an initial template motion, system 100 may receive sensor data from sensor device 200 that is recorded during the swing motion. For example, IMU 230 may record acceleration and/or orientation data along three or fewer axes during a particular swing motion. Sensor device 110 may transmit the IMU data to computing device 120, which may, in turn, store the IMU data for the swing motion as a motion profile. For example, the "ideal" template swing may be recorded in a clinical setting, such as with a trainer, and later recalled when a user practices without the trainer nearby.

In an embodiment, step 610 may include recording a motion, generating the template, storing the template in a networked server (e.g., server 130), and/or requesting the stored template for networked storage. In still further embodiments, step 610 may include receiving a motion profile that is generated from a software application, rather than recorded from a live motion. For example, in step 610, computing device 120 may receive a motion profile generated by process 1100, which is described later in this specification and depicted in FIG. 11. Additional combinations or intermittent processes may be used such that computing device 120 receives a data profile or a motion profile for use consistent with the remaining steps of process 600.

In step 615, process 600 may receive real-time sensor data. Computing device 120 may receive real-time data from sensor device 110. In some embodiments, computing device 120 may receive sensor data in real-time over a wireless transmission technology such as Bluetooth or Wi-Fi (e.g., using Bluetooth transceiver 352 and/or Wi-Fi transceiver 354). Computing device 120 may receive packets of data containing real-time data samples from one or more of internal sensor(s) 341 and/or external sensor(s) 344. For example, computing device 120 may receive one or more packets containing 1-10 samples of data for a given sensor over an interval of 1-5 milliseconds, with less than a 5 millisecond delay from capture by sensor device 110. The samples may be stored as time-value pairs in an array, such as sensor sample values paired with timestamp values in a list. In some embodiments, computing device 120 may continue to receive sensor data packets so long as sensor device 110 captures relevant data (e.g., as discussed with regard to step 810, step 820, and/or step 830 of FIG. 8 below).

In step 620, process 600 may calculate a test swing profile. Computing device 120 may aggregate received sensor data into a combined time-wise arrangement of sensor readings. In some embodiments, computing device 120 may create a new data structure organizing the sensor data for a given motion. The data structure may store an abbreviated form of raw sensor data with standardized metadata in a data object. For example, computing device 120 may receive raw sensor data having varying fidelity (e.g., differing sample rates and/or data precision). Computing device 120 may organize data such that the resulting class of data structures has consistent sampling rates and/or sample data with consistent resolution (e.g., values having the same number of significant figures). For example, computing device 120 may down-sample sensor data having a sampling rate greater than the standardized sampling rate or range of sampling rates for a given class or type of swing profile (e.g., a type of motion profile) data structures. For received sensor data having a sampling rate that is lower than a minimum sampling rate for a given class of swing profiles, computing device 120 may interpolate additional data points to achieve the desired sampling rate (e.g., using curve fitting or regression analysis).

In some embodiments, the swing profile (e.g., a data profile or motion profile) may include standardized metadata. For example, the swing profile class may include fields for standardized data analysis variables, such as mean and median values of the sensor data, as well as standard deviation, high value, low value, local minima and maxima, and points of inflection. Additional data analytics discussed throughout this disclosure may be stored as part of the swing profile.

In some embodiments, the calculations may include comparing the test swing profile to a reference profile, such as the template swing profile (e.g., from step 610). Computing device 120 may compare the two profiles to determine where the two profiles deviate and how much the two profiles deviate. In an embodiment, computing device 120 may generate a profile indicating the differences over time. Additional comparisons may be made consistent with the data profile and motion profile comparisons discussed in this disclosure.

In step 625, process 600 may provide feedback based on the calculations made in step 620. Feedback may include visual, tactile, and/or auditory signals directed to a user and/or third party. The feedback may be based on the calculated test swing profile, its associated metadata, or a comparison based on the same. The calculations from step 620 may act as triggers for feedback. For example, when a test swing profile deviates more than a predefined amount, system 100 may generate feedback. In another example, system 100 may generate feedback when the test motion profile matches certain criteria, such as an average or standard deviation value. Such values may be user-defined or pre-defined (e.g., from loading a template profile in step 610). Feedback may be provided to a user between 5 and 20 milliseconds from receiving the data from the sensors, for example.

In some embodiments, computing device 120 may provide feedback to a user. For example, computing device may generate a graphical user interface that displays an analysis of sensor data. The graphical user interface may depict different views of the swing motion, such as those depicted in user interface 700A and user interface 700B in FIGS. 7A and 7B.

Figure 7A:
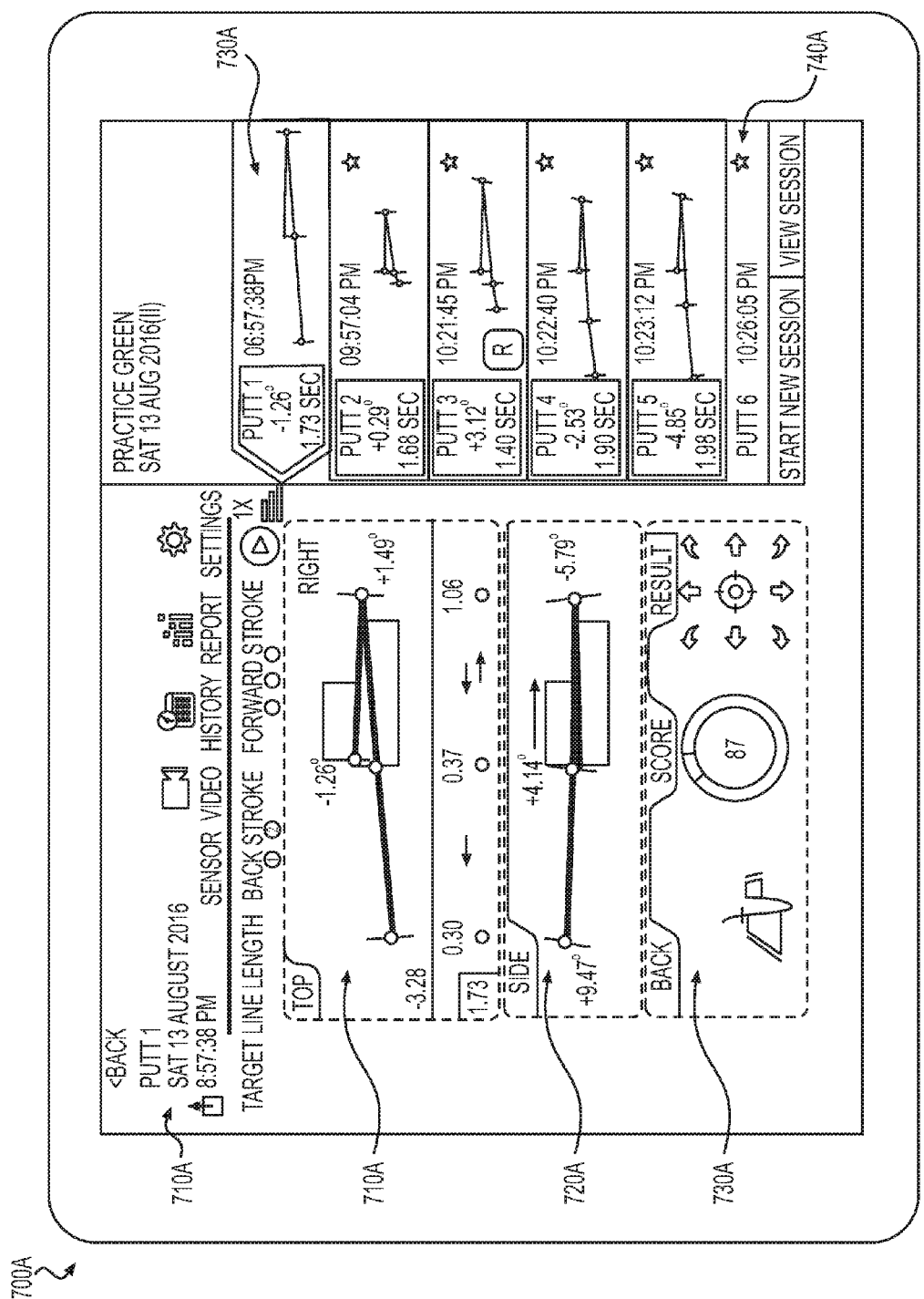
FIGS. 7A and 7B illustrate real-time data acquisition and feedback graphical user interfaces in accordance with some embodiments of the present disclosure.
Figure 7B:
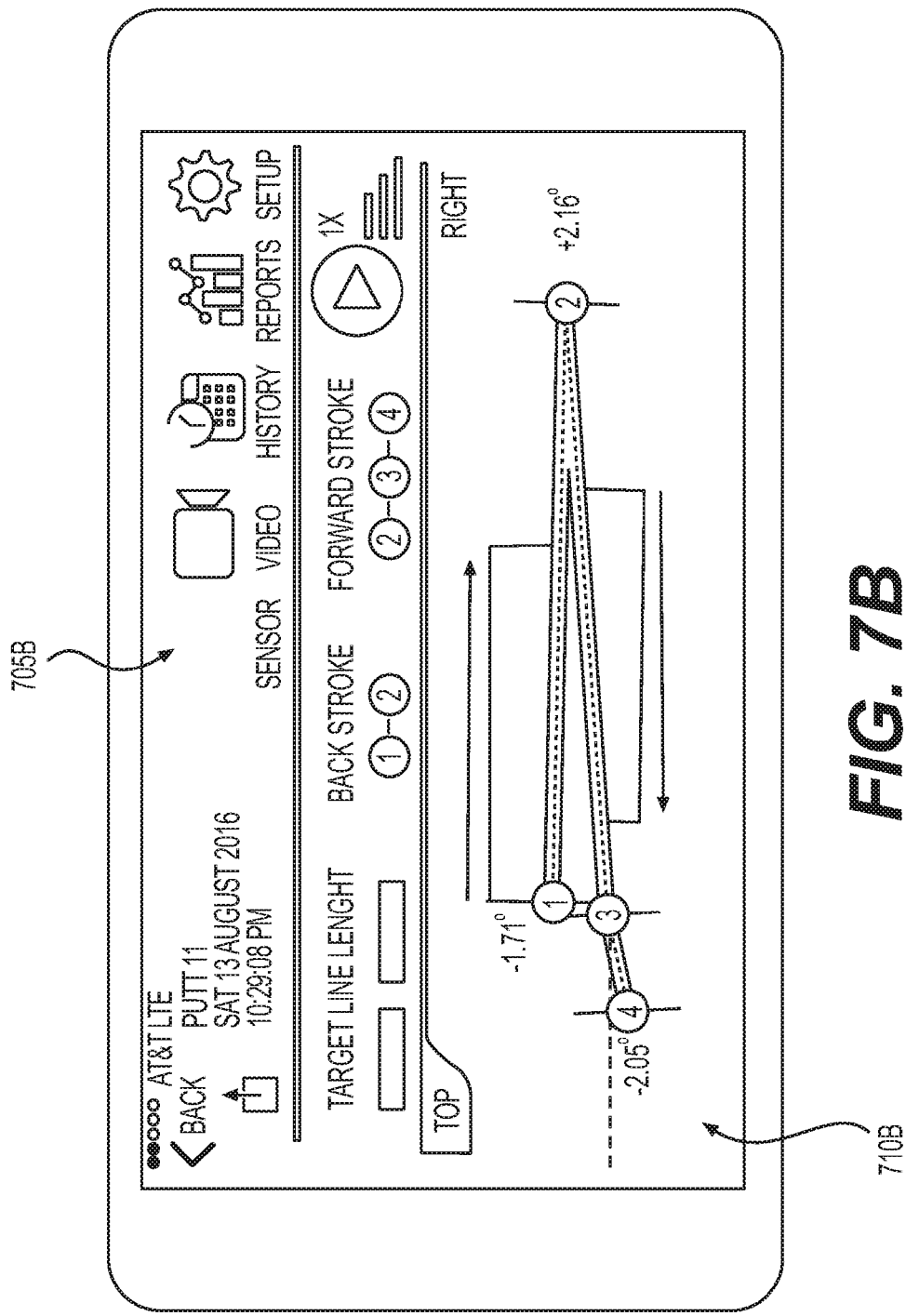

FIGS. 7A and 7B illustrate real-time data acquisition and feedback graphical user interfaces according to some embodiments of the present disclosure. FIG. 7A depicts graphical user interface 700A, which may include regions to depict real-time, relevant feedback as well as representations or abstractions of sensor data previously received from sensor device 110. In some embodiments, interface 700A may include one or more dimensional views that include a functional spatial map of the processed sensor data, such as top view region 710A, side view region 720A, and back view region 730A. Each of the plurality of views may display an elevation (e.g., side, top, back) of a golf motion (e.g., a golf putt, a golf swing) plotted on respective axes. In some embodiments, the depicted paths may be annotated or colored to convey additional data about the putt profile data. For example, the line path may be color coded to note the motion acceleration (e.g., green for accelerating and red for decelerating) or deviation for a template putt profile (e.g., red increasing in shade to correspond to the amount of deviation). Other color coding may be used to convey different putt or swing variables.

As shown, interface 700A also includes metadata display region 705A. This region may display the timestamp of the putt profile and various labels, such as an identification number and/or title for the motion profile. While not shown, region 705A may also include location data, such as GPS coordinates, a geographic region, and/or a hole number and corresponding golf course.

In addition to real-time data, interface 700A may also include a record of prior data. Region 740A may include a list of prior profiles, with selection region 730A indicating the selected putt profile for full display.

Turning to FIG. 7B, a smaller version of the user interface of a computing device (e.g., computing device 120) is shown. With smaller space, the user interface may show metadata display region 705B and top view region 710B at once. However, the user may interact with the user interface to retrieve additional data (e.g., the regions of interface 700A) via menus. For example, a user may scroll through different elevation views of the putt profile and select the depicted "BACK" arrow to return to a list of past recorded putt profiles.

Returning to FIG. 6, in some embodiments, step 625 may include sensor device 110 providing feedback to a user. Computing device 120 may transmit one or more signals to sensor device 110 to trigger output 320 based on calculations (e.g., from step 620). For example, computing device 120 may transmit (e.g., using wireless transceiver 250) an instruction to activate light(s) 322, speaker(s) 324, and/or tactile engine 326. In one example, when computing device 120 determines that the test swing profile matched the template swing profile, it may transmit a signal to display green lights. However, when the test swing profile deviates more than a specified amount, the instruction may activate red lights of sensor device 110. In another example, computing device 120 may transmit an instruction to sensor device 110 to have tactile engine 326 perform a particular vibration and/or have speaker(s) 324 play the sound of a crowd cheering when test swing profile meets certain criteria. Other triggers and combinations for feedback mechanisms may be used based on environmental conditions. For example, when system 100 determines that it is very bright outside, sensor device 110 may activate tactile engine 326, rather than or in addition to light(s) 322.

In other embodiments, sensor device 110 may locally perform calculations and initiate feedback without instructions from computing device 120. For example, processor 210 may perform the above-discussed functions of computing device 120 and locally initiate one of the discussed feedback mechanisms.

In step 630, process 600 may determine if additional data has been received. For example, system 100 may repeat one or more of step 615, step 620, and step 625 based on additional data corresponding to a new or ongoing sensor profile.

Figure 8:
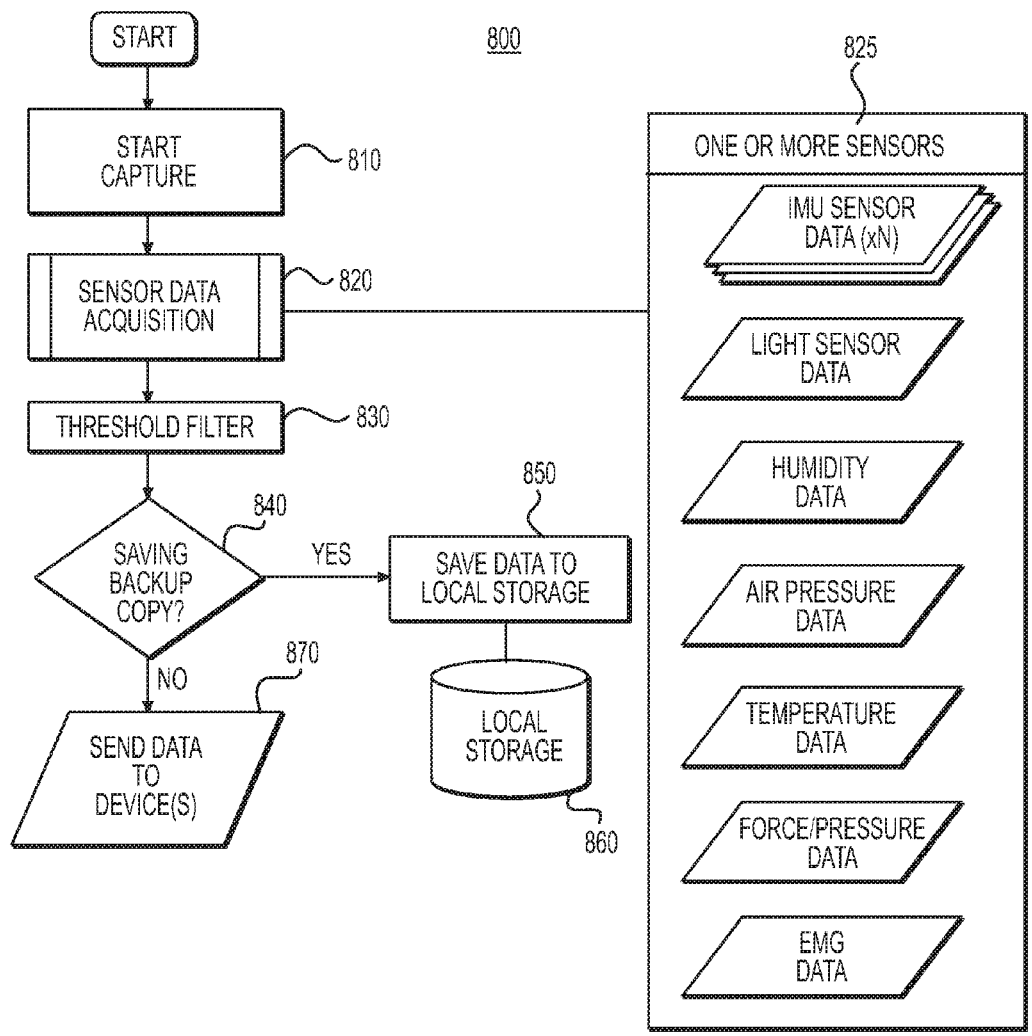
FIG. 8 is a flow diagram illustrating a real-time data acquisition and feedback process in accordance with some embodiments of the present disclosure.

FIG. 8 is a flow diagram illustrating a real-time data acquisition and feedback process 800 according to some embodiments of the present disclosure. The discussion below of process 800 references functions performed by sensor device 110. However, in some embodiments, certain functions may be performed by one or more alternative devices.

In step 810, process 800 may being capturing data. In some embodiments, sensor device 110 may identify particular sensors to sample data from. For example, processor 210 may identify IMU 230 for data capture.

In step 820, process 800 may acquire data from one or more sensors. In some embodiments, sensor device 110 may commence recording and processing of sensor data from one or more sensors 825 (e.g., IMU 230, sensor(s) 240). For example, sensor device 110 may record sensor readings in temporary storage over a predefined interval.

In step 830, process 800 may apply a threshold filter to acquired data. In some embodiments, sensor device 110 may evaluate whether the data meets certain qualifications for processing. Certain types of data may represent noise or other not useful data. For example, sensor device 110 may evaluate whether motion data corresponds to a golf swing, rather than errant non-swing movement of the club (e.g., walking with the club, placing the club in a golf bag, setting up to swing). Sensor device 110 may filter out movements that are determined to not correspond to a golf swing. In some embodiments the filter may calculate the amount of deviation and filter out data that is too noisy to represent a simple swing motion. For example, a series of quick random movements may represent the club bouncing around in the golf bag and, thus, may be discarded by sensor device 110. By comparison, a swing normally may include two continuous movements (e.g., the back swing and forward swing) that occur over a relatively standard range of time. In other embodiments step 830 may represent a simple filter where readings below a specified magnitude are filtered out. For example, sensor device 110 may identify minor movements that have acceleration values below a threshold amount and discard them. In still other embodiments, sensor device 110 may power down or enter a "hibernation" mode to conserve power when no satisfactory data is received.

In step 840, process 800 may determine whether a backup copy of the acquired data needs to be saved. In some embodiments, sensor device 110 may determine whether sufficient storage exists and/or whether preferences dictate that the sensor data should be archived locally.

In step 850, process 800 may transmit the acquired sensor data to local storage. For example, when sensor device 110 determines that preferences dictate that data be stored locally and detects an external storage device (e.g., step 840, "YES"), sensor device may save sensor data to local storage 860 (e.g., internal storage 316 and/or external storage 317).

In step 870, process 800 may transmit acquired sensor data to device(s). In some embodiments, sensor device 110 may transmit sensor data to computing device 120. For example, when accumulated sensor data reaches a predetermined threshold, such as a percentage of the amount of local storage 860 used, or a predetermined time duration, sensor device 110 may format and send acquired sensor data to computing device 120 for further processing (e.g., process 600 and/or process 900).

Figure 9:
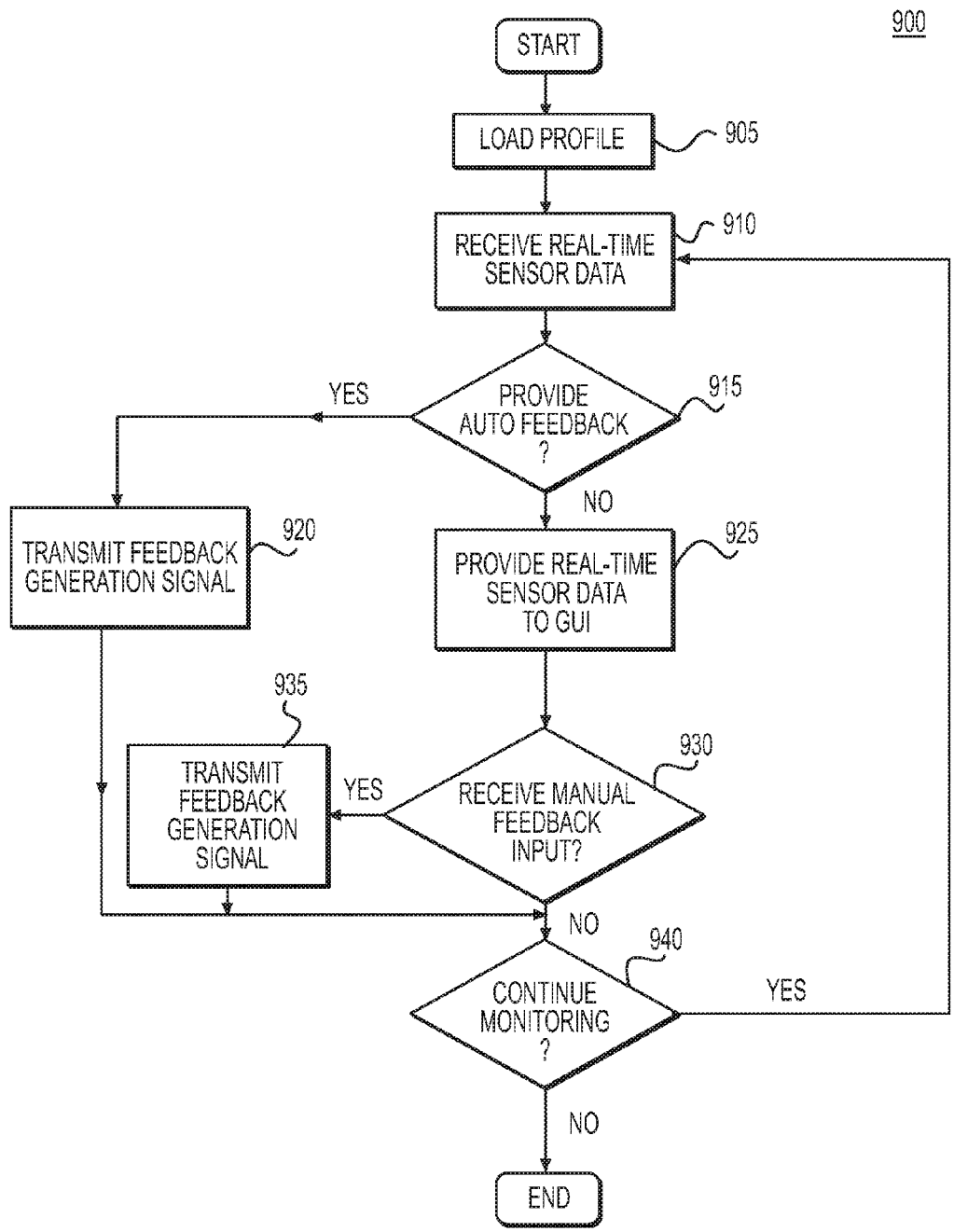
FIG. 9 is a flow diagram illustrating a real-time data acquisition and feedback process in accordance with some embodiments of the present disclosure.

FIG. 9 is a flow diagram illustrating a real-time data acquisition and feedback process 900 according to some embodiments of the present disclosure. Disclosed functions are discussed regarding computing device 120 below. However, additional devices may perform disclosed functions, in whole or part. For example, sensor device 110 may perform certain feedback calculations locally, rather than receiving an instruction from computing device 120 to do so.

In step 905, process 900 may load a user's profile. Computing device 120 may recall user data from networked or local storage. For example, computing device 120 may transmit a request including a user identifier for past data associated with the user. Based on the request, computing device 120 may receive past user data (e.g., data profiles), user preferences, and/or treatment plans. Treatment plans may include data profiles, such as motion profiles for particular treatment or therapeutic movements.

In step 910, process 900 may receive real-time sensor data. Computing device 120 may receive real-time data from one or more sensors. In some embodiments, computing device 120 may receive sensor data in real-time over a wireless transmission technology such as Bluetooth or Wi-Fi (e.g., using Bluetooth transceiver 352 and/or Wi-Fi transceiver 354). Computing device 120 may receive packets of data containing real-time data samples from one or more of internal sensor(s) 341 and/or external sensor(s) 344. For example, computing device 120 may receive one or more packets containing 1-10 samples of data for a given sensor over an interval of 1-5 milliseconds, with less than a 5-20 millisecond delay from capture by sensor device 110. The samples may be stored as time-value pairs in an array, such as sensor sample values paired with timestamp values in a list. In some embodiments, computing device 120 may continue to receive sensor data packets so long as sensor device 110 captures relevant data (e.g., as discussed with regard to step 810, step 820, and/or step 830 of FIG. 8).

In some embodiments, computing device 120 may receive multiple motion data streams simultaneously. The simultaneous streams may come from sensors that are co-located or located at different points on a user or object. In the example of co-located sensors, system 100 may receive the sensor data and interlace it to increase resolution of the data. For example, the sensor data streams may have the same sample interval, but system 100 may control the sampling time to offset each stream based on the number of streams to increase resolution. Computing device 120 may divide the sampling rate by the number of streams to calculate an offset amount. Computing device 120 may provide instructions to each sensor device 110 to begin sampling at a multiple of the offset amount such that no two sensor devices sample at the exact same time. Computing device 120 may combine the sample streams by interlacing the discrete data points based on their associated timestamp.

In the example of multiple motion streams from different locations, the sensor may be located at different portions of a user limb, such as at the user's wrist and bicep, for example to account for changes in orientation of the arm on either side of a user's elbow. Such an exemplary sensor arrangement may be used to measure the range of motion of a user's elbow and act as a goniometer. While an elbow is used as an example, additional joints may be similarly monitored, such as the orientation of the head relative to the torso for a user's neck, or measuring the range of motion of a knee, back, and/or hip. The range of motion of additional joints may be measured while not explicitly named here. Such an arrangement may advantageously provide more accurate range of motion data than typically measured with a goniometer because the sensor device take into account the relative orientation in three-axes, rather than being limited to an angle in a single dimension.

In other embodiments, systems and methods may obtain goniometric measurements with the use of only a single sensor device. For example, a single sensor device 110 may provide three-axis orientation data over time. The user may detachably affix sensor device 110 to a limb of a joint of interest, and sensor device 110 may transmit orientation data indicating the orientation of the limb over time. In this example, disclosed embodiments may assume that the body part opposite the sensor limb remain static for purposes of determining goniometer data and/or range of motion measurements. For example, the change in orientation of the single sensor device 110 may be used to calculate the range of motion by determining the magnitude of the origination data of a particular axis or combination of axes over time. Based on orientation data from multiple axes, computing device 120 may calculate an equation defining a three-dimensional plane (e.g., $ax+by+cz=0$) in which the motion takes place. Then, within that plane, computing device 120 may determine the number of degrees through which the orientation passes. Thus, even though a user's motion may not perfectly occur such that it only occurs along a single axis, such as when a user performs an arm raise while slightly bent over, computing device 120 may calculate the range of motion on a coordinate system normalized for the orientation of the body while a user performs a given motion.

Computing device 120 may create data profiles based on the real-time data received from various sensors. For example, computing device 120 may organize real-time data into standardized sampling rates and number of significant figures of measurement values. When necessary, computing device 120 may convert units of measurements to be consistent for all data profiles of the same type (e.g., to use metric units).

In creating data profiles, computing device 120 may manipulate the raw data received from sensor devices. For example, computing device 120 may discard data values above and/or below predefined maximum and/or minimum values. Computing device 120 may also fit a curve or polynomial function to the data, or perform dynamic time warping. When multiple sensor data streams are received, computing device 120 may triangulate the data from multiple streams to increase the accuracy and reduce the noise in the resulting data profile.

In some embodiments, computing device 120 may correlate real-time data from a plurality of sensor devices simultaneously in step 910. For example, computing device 120 may receive real-time blood-glucose level data from a connected insulin pump (e.g., one of external sensor(s) 344), real-time heart rate data (e.g., from an ECG sensor), real-time muscle electrical activity (e.g., from an EMG sensor), and motion data (e.g., from IMU 230). Computing device 120 may compare heart rate data and blood-glucose level data with acceleration data (e.g., indicating speed of repetitions, stride length, gait). Additional types of real-time data may be received and correlated, such as those discussed in other portions of this disclosure.

Process 900 may determine whether to transmit automatic feedback in step 915. Computing device 120 may compare the calculated data profile with various criteria. For example, computing device 120 may determine whether characteristics of the data profile, such as the average value, standard deviation, slope, and points of inflexion match criteria, such as criteria loaded from a user profile (e.g., step 905). In some embodiments, step 915 may include comparing the data profile to a template to determine how much the data deviates from a desired template data profile. For example, computing device 120 may compare the calculated data profile to a template data profile based on the amount of deviation, such as the average deviation amount, summed total deviation, or maximum deviation. Based on this comparison, computing device 120 may determine that automatic feedback should be provided, as well as what type of feedback to provide.

Disclosed embodiments may provide iterative instructional feedback. Computing device 120 may compare a test data profile to multiple template profiles to determine which template profile most closely matches the test profile. The comparison may be based on a least squares difference between the test and template curves. In other examples, the Fourier transform of the curves may be compared. Additional comparisons of data profiles may be used as described throughout this disclosure. Each template profile may be associated with a different type of feedback (if any), and based on which template is best matched, computing device 120 may determine it is necessary to provide feedback, including, in one example, which type of feedback to provide (e.g., auditory, tactile, visual). Such feedback may include an indication of the profile that the test data profile most closely matched and a quantitative "score" of the motion based on the deviation amount.

In step 920, process 900 may transmit a feedback generation signal. Based on received real-time data meeting certain qualifications (e.g., step 915, "YES"), computing device may transmit a signal to generate feedback, such as feedback at sensor device 110 using one or more of output 320. For example, responsive to determining that the average value of a particular sensor falls within a certain range, computing device 120 may transmit a signal to activate tactile engine 326 of sensor device 110.

In some embodiments, each criteria or qualification may be paired with a particular type of feedback. Such pairings may be stored in the user profile (e.g., retrieved in step 905). For example, when sensor data falls within a certain range, a predetermined type of feedback may be provided. In an embodiment where different templates are mapped to different types of feedback, computing device 120 may transmit the corresponding feedback instruction to sensor device 110. In an example, a physical therapy or practice exercise may have a template motion profile, as well as a motion profile that represents a likely incorrect movement, such as one that extends beyond a target range of motion or when a movement is performed too quickly. The user may wear one or more of sensor device 110 while performing the exercise movement. When the user's exercise movement results in a motion profile that matches the template motion profile more closely than the chronic incorrect motion profile, computing device 120 may transmit a signal to activate green lights at sensor device 110. Alternatively, when computing device 120 determines that the received sensor data results in a motion profile that more closely matches the chronic incorrect motion profile, computing device may transmit an instruction to vibrate and activate red lights at sensor device 110.

In another embodiment, a user may receive feedback grouped with multiple other users. For example, an exercise class may have multiple participants, each outfitted with one or more of sensor device 110. For example, each participant in a pilates class may wear sensor device 110. The class may be divided into two groups or "teams." Sensor device may aggregate data associated with form or pressure applied by each user and combine the readings (e.g., sum or average) for a "team reading" or "team score" that is displayed to all participants using a graphical user interface (e.g., a display connected to computing device 120). For example, sensor device 110 may transmit data indicating the orientation of particular extremities of a user, based on the orientation data (e.g., a motion profile), the form or technique of the user may be compared to the ideal technique (e.g., a test motion profile). The amount of deviation may be normalized or otherwise translated into a quantitative "score" for the individual. The scores may be calculated for a particular exercise, motion, or pose, over the course of an entire class, and/or over multiple classes.

In step 925, process 900 may provide real-time sensor data to a graphical user interface. In an embodiment, when automatic feedback criteria are not triggered (e.g., step 915, "NO"), computing device 120 may provide real-time sensor data to a graphical user interface. For example, when computing device 120 is a tablet computer, computing device may display data profiles on a touchscreen of the user interface. In some embodiments, the user interface may display analytics together with a selection area to provide feedback to user. For example, a coach, trainer, or therapist may hold a tablet that displays real-time analysis of a user walking, such as gait, tempo, and stride length. The user interface on the tablet may show accelerometer data in one or more dimensions, along with the individual metric scores. In an embodiment, the metric scores may be displayed in bold, italics, underlined, or in certain colors when the metric falls within a predetermined range.

Process 900 may determine whether manual feedback has been received in step 930. In an embodiment, the user interface of computing device 120 may provide an area to select user feedback. For example, a third party (e.g., a therapist, trainer, coach) may manually select the type of feedback and when to send it. The third party may be monitoring real-time data profiles and associated metrics and decide when to initiate feedback. For example, a trainer may determine that a light may be effective feedback at the beginning of a workout and later switch to tactile feedback when the user becomes fatigued.

While manual feedback (e.g., step 925) is shown as an alternative to automatic feedback (e.g., step 920), the two may be used in combination in some embodiments. For example, manual and automatic feedback may be transmitted simultaneously. In another example, automatic feedback (e.g., step 925) may supersede or cancel out automatic feedback. For example, a third party user may deactivate certain automatic feedback triggers while operating the user interface.

In an embodiment, system 100 may monitor the manual feedback, including the type and timing of the manual feedback to suggest an automated rule to provide feedback. For example, system 100 may capture the data profile and associated metrics that occur at each manual feedback request. System 100 may recognize trends in the timing and type of feedback. For example, system 100 may determine that the third party switched from using lights for feedback to tactile feedback halfway through the motion or exercise. In another example, system 100 may recognize that feedback was initiated when a particular metric dropped below a threshold, such as run tempo dropping below a certain number of steps per minute. In still other examples, system 100 may recognize variable thresholds imposed by manual feedback. For example, system 100 may analyze manual feedback to determine that a threshold cadence below 170 steps per minute was used by the third party for the first five minutes of a run, while a cadence falling below 185 steps per minute prompted feedback for the next ten minutes of the run. In still other examples, combinations of different types of data in multi-dimensional data profiles may be correlated for feedback, such as gait and cadence metrics being used to prompt feedback in combination.

In another embodiment, a single third party may provide manual feedback to multiple users. For example, multiple users may be equipped with sensor devices (e.g., sensor device 110), such as teammates (e.g., on a track or cross-country team). The third party (e.g., a coach of the team) may operate computing device 120 to provide manual feedback to individual users, a selected group of users (e.g., all males, all athletes having a specific height and/or weight, or all athletes specializing in a particular event, such as hurdles), or all users (e.g., the entire team). In some embodiments, computing device 120 may provide a graphical user interface that presents information for all users to the third party. Selected type(s) of metrics may be displayed with a user identifier in a single user interface.

For example, sensor devices (e.g., sensor device 110) on each member of the track team may transmit real-time heartrate data, oxygen levels, insole pressure data, and/or three-axis accelerometer data with a user identifier to a tablet computer (e.g., computing device 120) operated by a track coach. Computing device 120 may calculate, using the accelerometer data and insole pressure data, clinically evaluative running data for each team member during a training session, such as gait, cadence, and foot landing (e.g., heel strike or midfoot landing) data. Computing device 120 may display the user identifier with the associated data profile metrics (e.g., cadence, gait, foot landing evaluations) and personal health data in real-time. Computing device 120 may calculate and render a graphical representation of additional metrics, consistent with the other examples provided through this disclosure.

Computing device 120 may provide a graphical user interface that allows a third party (e.g., coach) to observe relevant data and highlight data of interest. For example, when metrics exceed team-wide and/or individualized thresholds, a graphical indication (e.g., color highlighting or bold font) may be used to highlight the particular metric and corresponding user to the third party in real-time. The graphical user interface of computing device 120 may reorder the listing of user's data to show the highlighted data at the top of a list of user data. In still further examples, computing device may calculate data for subsets of users. For example, computing device 120 may receive input defining a series of personal identifiers as belonging to a group. Computing device 120 may then calculate and display clinically relevant data for the group The user interface may then receive input from the third party (e.g., the coach using a touchscreen) to select a user or group of users to provide feedback to. Computing device 120 may receive a selection of one or more user identifiers, a group identifier, or all users as well as a type of feedback to transmit to each sensor device 110 for the selected users. For example, computing device 120 may receive an instruction to transmit an instruction to sensor devices worn by distance runners to generate a particular vibration pattern responsive to determining that their cadence fell below a desired threshold. Still further embodiments may allow the third party to select a subset of users to provide additional data, such as a live plot of a particular selected metric over time (e.g., cadence).

In another example, football players' helmets may be equipped with sensor device 110. Each sensor device 110 may transmit accelerometer data and EMG data to computing device 120, which may be operated by a third party, such as an assistant coach, trainer, or medical professional. Computing device 120 may calculate clinically relevant acceleration metrics for display on a graphical user interface. At the conclusion of each play, computing device 120 may highlight individuals who may warrant a detailed concussion analysis. For example, computing device 120 may include acceleration thresholds that are used to identify high impact events. Computing device 120 may further generate a time-wise correlation of the acceleration data, impact events, and electro-muscular activity (e.g., from the EMG sensor) to flag a particular user identifier to the third party using the graphical user interface. For example, a high impact event with excessive acceleration magnitude correlated with no EMG activity (e.g., "going limp") may be used to highlight individuals that may have suffered excessive trauma. Computing device 120 may generate or transmit an instruction to the sensor device 110 of the identified user to generate a sound or activate onboard lights so that the affected individual may be easily identified by teammates, training staff, or other medical professionals.

Process 900 may transmit a feedback generation signal in step 935. For example, computing device 120 may transmit an instruction to the corresponding sensor device 110 to initiate the feedback specified in step 930.

Process 900 may determine whether monitoring should continue in step 940. In an embodiment, process 900 may continue while sensors continue to provide real-time data. When a motion or exercise is complete, and sensor device 110 deactivates (e.g., step 940, "NO"), process 900 may end.

In some embodiments, process 900 may associate particular equipment with sensor data. For example, process 900 may be used to evaluate different shoes, apparel, balls, and other sports tools or equipment. Associated sensor data from a user performing a given activity may be used to quantitatively rate the equipment. For example, a user may run a lap on a track multiple times, and each time the user may run with a different pair of running shoes. Disclosed embodiments may receive sensor data, such as acceleration data, sole pressure data, and other data to calculate metrics for each different pair of shoes. By comparing the data profiles obtained while running with different shoes, computing device 120 may determine a quantitative score to evaluate each pair of shoes. For example, the score may represent a normalized aggregation of the difference in the test motion profiles for each shoe compared with a template motion profile of a most efficient running technique, the speed of the lap (e.g., adjusted based on the number of laps previously run), and personal health data (e.g., pulse rate, myographic muscle sensor data, oxygen levels). Additional variables may be used to evaluate the equipment consistent with this disclosure.

Figure 10:
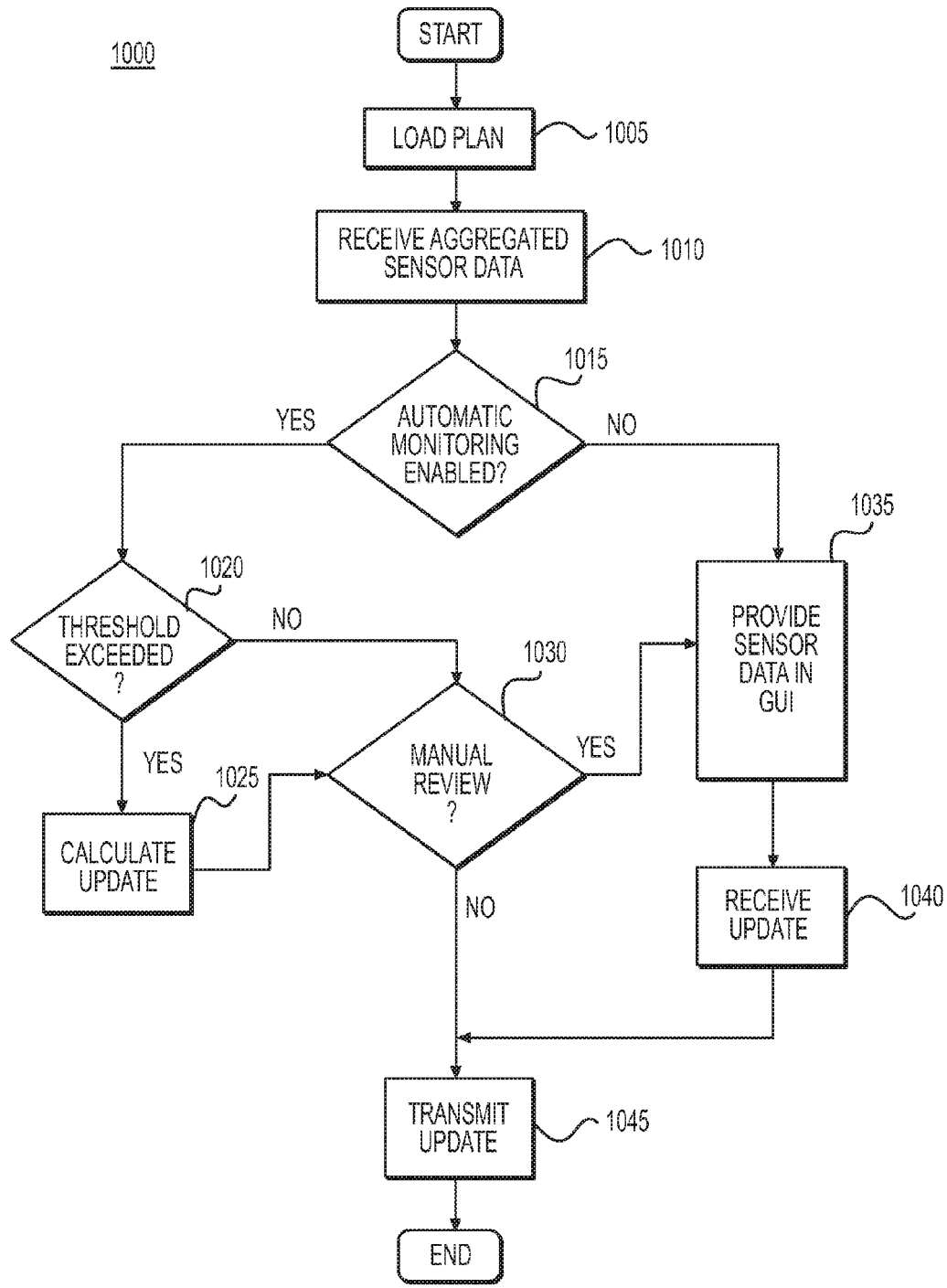
FIG. 10 is a flow diagram illustrating a data aggregation and update process in accordance with some embodiments of the present disclosure.

FIG. 10 is a flow diagram illustrating a data aggregation and update process 1000 according to some embodiments of the present disclosure. Process 1000 may describe a way to provide automatic adjustments to a user activity plan (e.g., an exercise plan, a rehabilitation plan, a training plan, a fitness plan, and/or a medical plan). For example, a user may have prescribed motion or a set of motions (potentially referred to as "exercises") based on a treatment or training plan, such as aerobic exercises, stretches, strength exercises, and/or joint movements. The plan of exercises may advance to achieve a desired goal by adding variations on the exercises (e.g., increased range of motion, increased repetitions, higher frequency, and/or new exercises altogether over time). However, system 100 may monitor exercises or prescribed motions (e.g., using sensor device 110) to evaluate user progress. For example, computing device 120 may upload data profiles recorded while a user performs the exercises and/or motions to server 130. Process 1000 describes a series of steps to provide manual adjustments (e.g., by a medical professional, a coach) and/or automatic adjustments to a user activity plan. For example, process 1000 may modify prescribed exercises and/or motions, add new exercises and/or motions, or alter repetitions. The steps described below are discussed primarily with regard to server 130. However, in other embodiments, the functions may be performed by other devices, such as computing device 120.

In step 1005, process 1000 may load a user plan. For example, server 130 may receive a user profile, including for example, an exercise plan, a rehabilitation plan, a training plan, a fitness plan, and/or a medical plan for a user. The plan may include biometric information, including the user's medical history. Such medical details may be coded so that server 130 may readily recognize certain conditions that may impact the user's performance of the exercises, such as the severity and type of muscle strain or bone fracture, a joint replacement, or disc herniation.

Process 1000 may receive aggregated sensor data in step 1010. Server 130 may receive data profiles obtained while the user performs the activities. For example, computing device 120 may upload calculated data profiles at regular intervals (e.g., hourly, daily) or when a session is complete (e.g., after not receiving additional data for a predetermined period of time, when determining that all prescribed exercises and/or motions in a plan have been completed for a given day). Server 130 may automatically add the received data to the clinical record of the user, for example, in an electronic medical record by interfacing with existing medical record database software.

In step 1015, process 1000 may determine whether automatic monitoring is enabled for the user plan. In some embodiments, server 130 may automatically monitor data uploaded by computing device 120. For example, the user, their coach, or their treating medical professional may enable server 130 to automatically track progress and provide feedback.

When automatic review is enabled (e.g., step 1015, "YES"), process 1000 may determine whether aggregated sensor data exceeds a threshold in step 1020. For example, server 130 may determine if the uploaded data profiles indicate whether the user is obtaining desired results. For example, server 130 may determine that a user's cadence drops below a desired threshold for the current exercise progression. In another example, server 130 may determine that a range of motion is increased beyond a target range, such as a user being able to lift arm raises higher than an initial expectation after shoulder surgery.

In step 1025, process 1000 may calculate an update to a user plan. When recorded data profiles fall below expectations (e.g., step 1020, "YES"), server 130 may identify more conservative graduations to a plan and/or alternative exercises, activities, motions, and/or movements. In the example of a slowing cadence, server 130 may modify the user plan to include additional short, high-tempo sprints. In the example of the arm raise accelerated range-of-motion progress, server 130 may increase the target range of motion for exercises in the user plan at a higher rate and/or add more advanced user exercises, or motion tasks.

In step 1030, process 1000 may determine whether manual review should occur. In some embodiments, whether or not automatic changes occur (e.g., step 1025), server 130 may determine that a third party should review the user's history. For example, when results raise particular flags, a trainer or medical professional may need to be notified and/or approve any plan modifications. In the example of arm raise accelerated range-of-motion progress, server 130 may determine that a particular item in the user's medical history may warrant consideration prior to implementing a more aggressive exercise plan and/or that the prescribed movements not be too advanced for the user. In certain embodiments, such as those relating to medical treatment, regulations or insurance plans may require that an authorized medical professional monitor and/or approve changes.

When server 130 determines manual review is needed for any of the reasons discussed above (e.g., step 1030, "YES"), process 1000 may provider sensor data in a graphical user interface in step 1035. For example, server 130 may transmit an electronic message to the third party (e.g., coach, doctor, trainer, therapist) to provide the user profile including any medical history, the treatment plan (e.g., prescribed exercises, rehabilitation exercises, fitness movements, other medical plan actions), the user progress (e.g., the data profiles), and/or the proposed modifications to the treatment plan. The third party may access the same information via an application and/or web portal. Server 130 may notify the third party of such updates via electronic mail, text message, automated phone call, or notifications in a web portal, application, or within normal operating notifications of mobile devices. The user interface may allow the third party to explore and view data profiles and the underlying raw data.

In step 1040, process 1000 may receive an update. In an embodiment, server 130 may receive an update to the plan from the third party via the user interface. For example, the third party may approve or modify suggested automatic changes to the plan. In an alternative example, the third party may negate proposed changes and/or include a message (e.g., text, video, audio) for the user.

In step 1045, process 1000 may transmit an update. In an embodiment, server 130 may transmit the automatic update without manual review (e.g., step 1030, "NO") and/or manual updates (e.g., step 1040). Server 130 may send a modified plan to computing device 120. The modified plan may include instructions, such as videos on how to perform new motion activities, an explanation of any alterations, and/or a message from the third party. For example, a doctor may include a note indicating that the user is performing a certain motion activity incorrectly, along with an instructional video overlaying a rendering of the user motion captured in the data profiles with the template motion.

Figure 11:
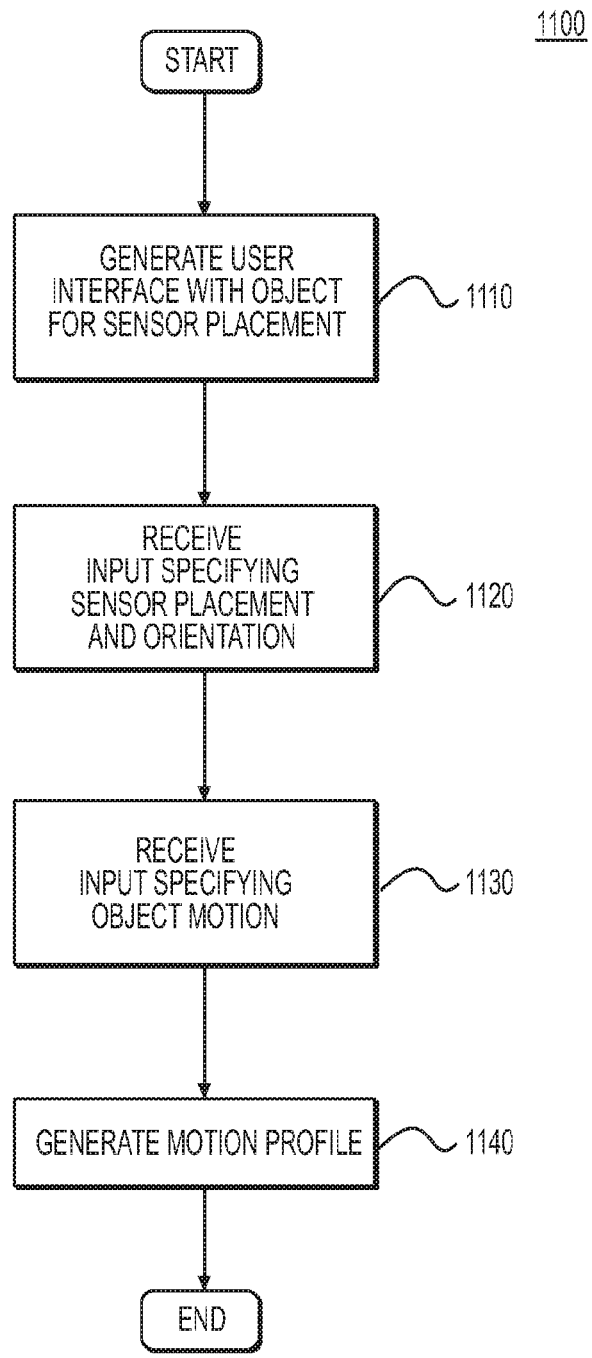
FIG. 11 is a flow diagram illustrating a motion profile generation process in accordance with some embodiments of the present disclosure.

FIG. 11 is a flow diagram illustrating a motion profile generation process according to some embodiments of the present disclosure. In some embodiments, template motion profiles may be generated by recording a person performing the "ideal" template motion while wearing a sensor at a certain location. However, in other embodiments, it may be desirable to electronically generate a motion profile for a specific motion, such as when a person is not available to perform the "ideal" motion. Process 1100 describes steps that allow a user (e.g., the sensor wearer) and/or a third party (e.g., a doctor, trainer, coach, therapist) to electronically create a motion profile without the need to record a person performing the template motion ideally.

In step 1110, process 1100 may generate a user interface for sensor placement on an object. System 100 (e.g., computing device 120) may render a human body in two or three dimensions. System 100 may store the location as coordinates in three-dimensions. In an embodiment, system 100 may customize the rendering of the human body based on measurement input, for example, so that the rendering more closely matches the user's body. In an alternative embodiment, system 100 may receive a three-dimensional scan of a user's body and process the scan data to generate a rendering.

In step 1120, process 1100 may receive input specifying sensor placement and orientation on an object. The user interface may allow a user to input an indication of a location on the human body where the sensor will be worn while performing the motion. In some embodiments, the user interface will allow the user to specify the orientation of the user device at the desired location.

In step 1130, process 1100 may receive input specifying motion of the object. In an embodiment, the user interface may render joints of the human body and their respective movements. For example, the user interface may limit movement of the portion of the human body depending on whether a joint is a hinge joint, a ball and socket joint, or a pivot joint. The user interface may allow the user to select and move renderings of the human body. For example, the user interface may receive input selecting and dragging a certain part of the body. In another example, the user interface may select beginning and ending positions, with computing device 120 interpolating the intermittent positions. In still another example, the user interface may allow a user to select a particular joint, input the axes and degrees of movement of the joint. After that movement is created, the system may allow the user to select another joint (or the same joint) and input other axes and degrees of movement. In this example, the user interface may allow the user to string together multiple segments to form a single motion, which the user interface may display in a timeline.

Process 1100 may generate a motion profile in step 1140. Computing device 120 may calculate the movement of the sensor device based on the motion the user describes at the interface. In an embodiment, computing device 120 may determine the path taken by sensor device 110 based on where sensor device 110 is located on the rendered human being and the movement of the rendered body. Based on the movement, computing device 120 may extrapolate the orientation and acceleration of the sensor device in three-dimensions over time, resulting in a motion profile for the motion described by the user in the user interface.

FIGS. 12A and 12B illustrate real-time data acquisition and feedback graphical user interfaces according to some embodiments of the present disclosure. Interface 1200A and interface 1200B may be shown on computing device 120 (e.g., a computer, tablet, smartphone).

Interface 1200A illustrates an exemplary user interface to select a sensor location on rendered body 1260A (e.g., step 1120). As shown, dialog region 1210A allows a user to move a rendering of sensor device 110 from its location 1240A in the dialog box, to position 1245A on rendered body 1260A. In the depicted example, cursor 1270A may be used to drag the sensor device rendering, releasing the cursor at position 1275A. In an embodiment, user interface 1200A allows a user to add additional sensors (e.g., using selection region 1220A). When all desired sensors are added, the user interface allows the user to confirm that step 1120 is complete in selection region 1230A.

Interface 1200B illustrates an exemplary user interface for specifying a movement of the rendered body (e.g., step 1130). As shown, a user may select a joint (e.g., icon 1240B) on rendered body 1260B for movement. Cursor 1270B may move the rendered portion of the body to the desired end position (or intermittent position) of a movement. Alternatively, dialog 12808 may allow a user to specify a particular angle for a joint position of a movement. In an embodiment, interface 1200B may depict the rendered body's start position 1250B with sensor start position 1275B, and overlay rendered body's end position 1255B with sensor end position 1265B. As shown the elbow also straightens between start and end positions. Therefore, the depicted motion may have an intermittent motion where the elbow straightens, such as either before beginning the shoulder movement or during the shoulder movement. As shown, dialog region 1210B allows a user in add such an additional movement. Selection region 1220B allows a user to select an additional movement, such as on an additional joint, while selection region 1230B confirms completion of the desired movement, triggering calculating the motion profile (e.g., step 1140).

It is intended that the disclosure and examples be considered as exemplary only, with a true scope and spirit of disclosed embodiments being indicated by the following claims.

What is claimed is:

1. A method for monitoring motion parameters and providing near-instantaneous user feedback from real-time motion sensor data comprising:

loading a template motion profile, the template motion profile describing a multi-dimensional representation of acceleration and orientation over time;

receiving, from one or more inertial measurement units, real-time sensor data from a motion sensor while a user performs a test motion with equipment, the motion sensor being mounted on equipment or affixed to the user, wherein receiving the real-time sensor data from the motion sensor includes:

receiving real-time sensor data from a plurality of sensors, the sensor data measuring a common metric and being received from each of the plurality of sensors at a common frequency and a unique offset based on the frequency and number of the plurality of sensors; and combining the real-time sensor data from the plurality of sensors by interlacing the sensor data, the interlacing resulting in the test motion profile having a sampling rate that is higher than a sampling rate of any one of the plurality of sensors;

calculating a test motion profile based on the real-time sensor data, the test motion profile describing a multi-dimensional representation of the test motion performed by the user;

comparing the template motion profile to the test motion profile to determine a deviation amount for the test motion profile indicating how the test motion deviated from the template motion profile using one or more of: a Fourier transform and a least squares difference calculation; and providing a graphical user interface that displays, and allows the user to manipulate a viewing angle of, a multi-dimensional rendering of the test motion profile, where the graphical user interface further displays the deviation amount in relation to the multi-dimensional rendering of the test motion profile.

2. The method of claim 1, wherein the equipment is a golf club, and the motion sensor is mounted on a shaft of the golf club at or below the base of a grip of the golf club.

3. The method of claim 2, further comprising:
providing, responsive to the comparing, real-time feedback to the user through the motion sensor mounted on the golf club based on the deviation amount.

4. The method of claim 1, further comprising:
storing the test motion profile with a plurality of additional test motion profiles,
calculating an average test motion profile for a given session,
determining differences between the average test motion profiles over time, and
providing a graphical demonstration of the differences to the user.

5. The method of claim 1, further comprising:
receiving GPS data,
identifying a geographic location based on the GPS data, and
indexing the test motion profile according to the identified geographic location.

6. The method of claim 1, further comprising:
determining, responsive to receiving the real-time sensor data, that the received real-time sensor data needs to be calibrated;
transmitting an instruction to the motion sensor to initiate a calibration procedure that includes the motion sensor aligning axes and adjusting scaling factors to increase accuracy in position and orientation data and providing an indication to the user that the calibration procedure is taking place; and
receiving, after the motion sensor has calibrated, calibrated real-time sensor data from the motion sensor while a user performs a test motion.

7. The method of claim 1, wherein the motion sensor includes a plurality of discrete motion sensor devices that each include one or more inertial measurement units and a tactile engine to provide haptic feedback, and the method further comprises:
identifying, based on at least the deviation amount for the test motion profile, a single discrete motion sensor device from the plurality of discrete motion sensor devices to provide haptic feedback;
transmitting an instruction to the identified single discrete motion sensor device causing the identified single discrete motion sensor device to provide haptic feedback to the user using the respective tactile engine of the identified single discrete motion sensor device.

8. The method of claim 1, wherein
the template motion profile further includes measurements of a plurality of additional template characteristics over time, the plurality of additional template characteristics including two or more of: elevation, temperature, humidity, and light intensity; and
the test motion profile based on the real-time sensor data includes an additional test characteristic measurement over time from the test motion performed by the user, the additional test characteristic measurement including two or more of elevation, temperature, light intensity, and pressure.

9. The method of claim 1, further comprising:
loading a plurality of template motion profiles, the template motion profiles each describing a multi-dimensional representation of acceleration and orientation over time and each having an associated feedback type, the associated feedback type being unique for each of the template motion profiles and including one or more of auditory, haptic, and visual feedback;
comparing the plurality of template motion profiles to the test motion profile to identify a matching template motion profile of the plurality of template motion profile based on one or more of: a Fourier transform and a least squares difference calculation; and
transmitting an instruction to the motion sensor to cause the motion sensor to provide feedback to the user based on the associated feedback type corresponding to the matching template motion profile.

10. The method of claim 1, further comprising:
loading a plurality of template motion profiles, the template motion profiles each describing a multi-dimensional representation of acceleration and orientation over time and each having an associated control function of a medical device,
the medical device being an insulin pump, a pacemaker, a cardiac defibrillator, a gastric stimulator, a deep brain neurostimulator, or a cochlear implant, and
the associated control function being unique for each of the template motion profiles;
comparing the plurality of template motion profiles to the test motion profile to identify a matching template motion profile of the plurality of template motion profile based on one or more of: a Fourier transform and a least squares difference calculation;
identifying, based on the matching template motion profile, the respective associated control function of the medical device; and
transmitting the identified associated control function to the medical device.

11. A system for monitoring motion parameters and providing near-instantaneous user feedback from real-time motion sensor data comprising:
a motion sensor that includes one or more inertial measurement units, wherein the motion sensor includes a plurality of sensors;
a non-transitory computer readable storage medium configured to store instructions; and
one or more processors programmed to execute the stored instructions to:
load a template motion profile, the template motion profile describing a multi-dimensional representation of acceleration and orientation over time;
receive real-time sensor data from the motion sensor detachably fixed to a user while a user performs a test motion, wherein the one or more processors receive the real-time sensor data from the motion sensor by:

receiving real-time sensor data from the plurality of sensors, the sensor data measuring a common metric and being received from each of the plurality of sensors at a common frequency and a unique offset based on the frequency and number of the plurality of sensors, each sensor of the plurality of sensors having a different offset; and combining the real-time sensor data from the plurality of sensors by interlacing the sensor data, the interlacing resulting in the test motion profile having a sampling rate that is higher than a sampling rate of any one of the plurality of sensors;

calculate a test motion profile based on the real-time sensor data, the test motion profile describing a multi-dimensional representation of the test motion performed by the user;

compare the template motion profile to the test motion profile to determine a deviation amount for the test motion profile indicating how the test motion deviated from the template motion profile using one or more of: a Fourier transform and a least squares difference calculation; and provide a graphical user interface that displays, and allows the user to manipulate a viewing angle of, a multi-dimensional rendering of the test motion profile, where the graphical user interface further displays the deviation amount in relation to the multi-dimensional rendering of the test motion profile.

12. The system of claim 11, wherein the one or more processors are programmed to execute the stored instructions further to:

transmit, based on the deviation amount, an instruction to the motion sensor to provide one or more of haptic feedback, auditory feedback, or visual feedback to the user.

13. The system of claim 12, wherein the one or more processors programmed to execute the stored instructions further to:

provide, responsive to the comparing, real-time feedback to the user through the motion sensor based on the deviation amount.

14. The system of claim 11, wherein the one or more processors programmed to execute the stored instructions further to:

store the test motion profile with a plurality of additional test motion profiles, calculate an average test motion profile for a given session, determine differences between the average test motion profiles over time, and provide a graphical demonstration of the differences to the user.

15. The system of claim 11, wherein the one or more processors programmed to execute the stored instructions further to:

receive GPS data, identify a geographic location based on the GPS data, and index the test motion profile according to the identified geographic location.

16. A non-transitory computer-readable medium storing instructions that, when executed by one or more processors, cause the one or more processors to perform operations comprising:

loading a template motion profile, the template motion profile describing a multi-dimensional representation of acceleration and orientation over time;

receiving, from one or more inertial measurement units, real-time sensor data from a motion sensor detachably fixed to a user while a user performs a test motion, wherein receiving the real-time sensor data from the motion sensor includes:

receiving real-time sensor data from a plurality of sensors, the sensor data measuring a common metric and being received from each of the plurality of sensors at a common frequency and a unique offset based on the frequency and number of the plurality of sensors, each sensor of the plurality of sensors having a different offset; and combining the real-time sensor data from the plurality of sensors by interlacing the sensor data, the interlacing resulting in the test motion profile having a sampling rate that is higher than a sampling rate of any one of the plurality of sensors;

calculating a test motion profile based on the real-time sensor data, the test motion profile describing a multi-dimensional representation of the test motion performed by the user;

comparing the template motion profile to the test motion profile to determine a deviation amount for the test motion profile indicating how the test motion deviated from the template motion profile using one or more of: a Fourier transform and a least squares difference calculation; and providing a graphical user interface that displays, and allows the user to manipulate a viewing angle of, a multi-dimensional rendering of the test motion profile, where the graphical user interface further displays the deviation amount in relation to the multi-dimensional rendering of the test motion profile.

17. The medium of claim 16, the operations further comprising:

transmitting, based on the deviation amount, an instruction to the motion sensor to provide one or more of haptic feedback, auditory feedback, or visual feedback to the user.

18. The medium of claim 17, the operations further comprising:

storing the test motion profile with a plurality of additional test motion profiles, calculating an average test motion profile for a given session, determining differences between the average test motion profiles over time, and providing a graphical demonstration of the differences to the user.

19. The medium of claim 17, the operations further comprising:

providing, responsive to the comparing, real-time feedback to the user through the motion sensor based on the deviation amount.

20. The medium of claim 16, the operations further comprising:

receiving GPS data, identifying a geographic location based on the GPS data, and indexing the test motion profile according to the identified geographic location.

* * * * *